(12) United States Patent
Marion

(10) Patent No.: US 9,138,282 B2
(45) Date of Patent: Sep. 22, 2015

(54) METHOD AND SYSTEM OF AN ELECTROSURGICAL CONTROLLER WITH WAVE-SHAPING

(75) Inventor: Duane W. Marion, Santa Clara, CA (US)

(73) Assignee: ArthroCare Corporation, Austin, TX (US)

( * ) Notice: Subject to any disclaimer, the term of this patent is extended or adjusted under 35 U.S.C. 154(b) by 434 days.

(21) Appl. No.: 13/559,729

(22) Filed: Jul. 27, 2012

(65) Prior Publication Data

US 2012/0296328 A1    Nov. 22, 2012

Related U.S. Application Data

(62) Division of application No. 12/486,013, filed on Jun. 17, 2009, now Pat. No. 8,257,350.

(51) Int. Cl.
*A61B 18/12* (2006.01)

(52) U.S. Cl.
CPC ..... *A61B 18/1206* (2013.01); *A61B 2018/1286* (2013.01); *A61B 2218/002* (2013.01); *A61B 2218/007* (2013.01)

(58) Field of Classification Search
CPC ............... A61B 2018/1286; A61B 2018/1206; A61B 2018/00767; A61B 2018/00755
USPC .................................................... 606/34–38
See application file for complete search history.

(56) References Cited

U.S. PATENT DOCUMENTS

| | | | |
|---|---|---|---|
| 2,050,904 A | 4/1936 | Trice | 219/31 |
| 2,056,377 A | 10/1939 | Wappler | 125/303 |
| 2,611,365 A | 9/1952 | Rubens | 606/42 |
| 3,434,476 A | 3/1969 | Shaw et al. | 606/22 |
| 3,633,425 A | 1/1972 | Sanford | 73/356 |
| 3,707,149 A | 12/1972 | Hao et al. | 128/303.14 |
| 3,718,617 A | 2/1973 | Royal | 260/30.4 |

(Continued)

FOREIGN PATENT DOCUMENTS

| | | | | |
|---|---|---|---|---|
| DE | 3119735 | | 1/1983 | A61B 17/39 |
| DE | 3930451 A1 | | 3/1991 | A61B 17/39 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Jaymi Della
(74) *Attorney, Agent, or Firm* — Norman F. Hainer, Jr.; David A. Warmbold

(57) ABSTRACT

An electrosurgical controller with wave-shaping. At least some embodiments are methods including generating an alternating current (AC) voltage signal within an electrosurgical controller. The generating may be by inducing an intermediate AC voltage signal on a secondary winding of a first transformer, and wave-shaping the intermediate AC voltage signal by a second winding of a second transformer coupled to the first transformer, and thereby creating a final AC voltage signal. Thereafter, the method includes applying the final AC voltage signal to electrical pins of a connector configured to couple to an electrosurgical wand.

11 Claims, 9 Drawing Sheets

(56) References Cited

U.S. PATENT DOCUMENTS

| | | | |
|---|---|---|---|
| 3,815,604 A | 6/1974 | O'Malley et al. | 128/305 |
| 3,828,780 A | 8/1974 | Morrison, Jr. et al. | 128/275 |
| 3,901,242 A | 8/1975 | Storz | 128/303 |
| 3,920,021 A | 11/1975 | Hiltebrandt | 128/303 |
| 3,939,839 A | 2/1976 | Curtiss | 128/303 |
| 3,963,030 A | 6/1976 | Newton | 606/40 |
| 3,964,487 A | 6/1976 | Judson | 606/39 |
| 3,970,088 A | 7/1976 | Morrison | 128/303 |
| 4,033,351 A | 7/1977 | Hetzel | 606/48 |
| 4,040,426 A | 8/1977 | Morrison, Jr. | 128/303 |
| 4,043,342 A | 8/1977 | Morrison, Jr. | 128/303 |
| 4,074,718 A | 2/1978 | Morrison, Jr. | 128/303 |
| 4,092,986 A | 6/1978 | Schneiderman | 128/303 |
| D249,549 S | 9/1978 | Pike | D24/144 |
| 4,114,623 A | 9/1978 | Meinke et al. | 606/39 |
| 4,116,198 A | 9/1978 | Roos | 128/303 |
| 4,181,131 A | 1/1980 | Ogiu | 128/303 |
| 4,184,492 A | 1/1980 | Meinke et al. | 128/303 |
| 4,202,337 A | 5/1980 | Hren et al. | 128/303 |
| 4,228,800 A | 10/1980 | Degler, Jr. et al. | 128/303 |
| 4,232,676 A | 11/1980 | Herczog | 128/303 |
| 4,240,441 A | 12/1980 | Khalil | 600/505 |
| 4,248,231 A | 2/1981 | Herczog et al. | 128/303 |
| 4,301,801 A | 11/1981 | Schneiderman | 606/38 |
| 4,326,529 A | 4/1982 | Doss et al. | 128/303 |
| 4,346,715 A | 8/1982 | Gammell | 607/99 |
| 4,363,324 A | 12/1982 | Kusserow | 607/64 |
| 4,378,801 A | 4/1983 | Oosten | 606/37 |
| 4,381,007 A | 4/1983 | Doss | 128/303 |
| 4,418,692 A | 12/1983 | Guay | 606/42 |
| 4,474,179 A | 10/1984 | Koch | 606/40 |
| 4,476,862 A | 10/1984 | Pao | 128/303 |
| 4,509,532 A | 4/1985 | DeVries | 128/736 |
| 4,520,818 A | 6/1985 | Mickiewicz | 606/40 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,572,206 A | 2/1986 | Geddes et al. | 600/505 |
| 4,580,557 A | 4/1986 | Hertzmann | 606/12 |
| 4,587,975 A | 5/1986 | Salo et al. | 600/506 |
| 4,590,934 A | 5/1986 | Malis et al. | 128/303 |
| 4,593,691 A | 6/1986 | Lindstrom et al. | 128/303 |
| 4,658,817 A | 4/1987 | Hardy | 606/14 |
| 4,660,571 A | 4/1987 | Hess et al. | 128/784 |
| 4,674,499 A | 6/1987 | Pao | 128/303 |
| 4,682,596 A | 7/1987 | Bales et al. | 128/303 |
| 4,706,667 A | 11/1987 | Roos | 128/303 |
| 4,709,698 A | 12/1987 | Johnston et al. | 606/41 |
| 4,727,874 A | 3/1988 | Bowers et al. | 128/303 |
| 4,750,902 A | 6/1988 | Wuchinich et al. | 604/22 |
| 4,765,331 A | 8/1988 | Petruzzi et al. | 128/303 |
| 4,785,823 A | 11/1988 | Eggers et al. | 128/692 |
| 4,805,616 A | 2/1989 | Pao | 128/303 |
| 4,823,791 A | 4/1989 | D'Amelio et al. | 123/303 |
| 4,832,048 A | 5/1989 | Cohen | 128/786 |
| 4,846,179 A | 7/1989 | O'Connor | 607/72 |
| 4,860,752 A | 8/1989 | Turner | 607/102 |
| 4,898,169 A | 2/1990 | Norman et al. | 606/42 |
| 4,907,589 A | 3/1990 | Cosman | 606/34 |
| 4,920,978 A | 5/1990 | Colvin | 128/784 |
| 4,931,047 A | 6/1990 | Broadwin et al. | 604/22 |
| 4,936,281 A | 6/1990 | Stasz | 128/660 |
| 4,936,301 A | 6/1990 | Rexroth et al. | 606/45 |
| 4,943,290 A | 7/1990 | Rexroth et al. | 606/45 |
| 4,955,377 A | 9/1990 | Lennox et al. | 607/105 |
| 4,966,597 A | 10/1990 | Cosman | 606/50 |
| 4,967,765 A | 11/1990 | Turner et al. | 128/785 |
| 4,976,711 A | 12/1990 | Parins et al. | 606/48 |
| 4,979,948 A | 12/1990 | Geddes et al. | 606/33 |
| 4,998,933 A | 3/1991 | Eggers et al. | 606/41 |
| 5,007,908 A | 4/1991 | Rydell | 606/47 |
| 5,009,656 A | 4/1991 | Reimels | 606/48 |
| 5,026,387 A | 6/1991 | Thomas | 606/169 |
| 5,035,696 A | 7/1991 | Rydell | 606/47 |
| 5,047,026 A | 9/1991 | Rydell | 606/48 |
| 5,047,027 A | 9/1991 | Rydell | 606/48 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,080,660 A | 1/1992 | Buelna | 606/45 |
| 5,083,565 A | 1/1992 | Parins | 600/374 |
| 5,084,044 A | 1/1992 | Quint | 606/27 |
| 5,085,659 A | 2/1992 | Rydell | 606/47 |
| 5,088,997 A | 2/1992 | Delahuerga et al. | 606/42 |
| 5,092,339 A | 3/1992 | Geddes et al. | 606/505 |
| 5,098,431 A | 3/1992 | Rydell | 606/48 |
| 5,099,840 A | 3/1992 | Goble | 128/422 |
| 5,102,410 A | 4/1992 | Dressel | 606/15 |
| 5,108,391 A | 4/1992 | Flachenecker et al. | 606/38 |
| RE33,925 E | 5/1992 | Bales et al. | 606/48 |
| 5,112,330 A | 5/1992 | Nishigaki et al. | 606/46 |
| 5,122,138 A | 6/1992 | Manwaring | 606/46 |
| 5,125,928 A | 6/1992 | Parins et al. | 606/48 |
| 5,156,151 A | 10/1992 | Imran | 600/375 |
| 5,167,659 A | 12/1992 | Ohtomo et al. | 606/40 |
| 5,171,311 A | 12/1992 | Rydell et al. | 606/48 |
| 5,174,304 A | 12/1992 | Latina et al. | 607/141 |
| 5,178,620 A | 1/1993 | Eggers et al. | 606/41 |
| 5,183,338 A | 2/1993 | Wickersheim et al. | 374/131 |
| 5,190,517 A | 3/1993 | Zieve et al. | 604/22 |
| 5,192,280 A | 3/1993 | Parins | 606/48 |
| 5,195,959 A | 3/1993 | Smith | 604/34 |
| 5,197,466 A | 3/1993 | Marchosky et al. | 128/399 |
| 5,197,963 A | 3/1993 | Parins | 606/46 |
| 5,207,675 A | 5/1993 | Canady | 606/40 |
| 5,217,457 A | 6/1993 | Delahuerga et al. | 606/42 |
| 5,217,459 A | 6/1993 | Kamerling | 606/48 |
| 5,249,585 A | 10/1993 | Turner et al. | 607/99 |
| 5,255,980 A | 10/1993 | Thomas et al. | 374/161 |
| 5,261,410 A | 11/1993 | Alfano et al. | 600/475 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,277,201 A | 1/1994 | Stern | 607/98 |
| 5,281,216 A | 1/1994 | Klicek | 606/42 |
| 5,281,218 A | 1/1994 | Imran | 606/41 |
| 5,282,799 A | 2/1994 | Rydell | 606/48 |
| 5,290,282 A | 3/1994 | Casscells | 606/29 |
| 5,300,069 A | 4/1994 | Hunsberger et al. | 606/37 |
| 5,306,238 A | 4/1994 | Fleenor | 606/42 |
| 5,312,400 A | 5/1994 | Bales et al. | 606/41 |
| 5,314,406 A | 5/1994 | Arias et al. | 604/21 |
| 5,318,563 A | 6/1994 | Malis et al. | 606/38 |
| 5,324,254 A | 6/1994 | Phillips | 604/21 |
| 5,330,470 A | 7/1994 | Hagen | 606/42 |
| 5,334,140 A | 8/1994 | Phillips | 604/35 |
| 5,334,183 A | 8/1994 | Wuchinich | 606/46 |
| 5,334,193 A | 8/1994 | Nardella | 606/41 |
| 5,336,220 A | 8/1994 | Ryan et al. | 604/22 |
| 5,336,443 A | 8/1994 | Odashima | 252/511 |
| 5,342,357 A | 8/1994 | Nardella | 606/40 |
| 5,348,554 A | 9/1994 | Imran et al. | 606/41 |
| 5,366,443 A | 11/1994 | Eggers et al. | 604/114 |
| 5,370,675 A | 12/1994 | Edwards et al. | 607/101 |
| 5,374,261 A | 12/1994 | Yoon | 604/385.01 |
| 5,375,588 A | 12/1994 | Yoon | 128/4 |
| 5,380,277 A | 1/1995 | Phillips | 604/33 |
| 5,380,316 A | 1/1995 | Aita | 606/7 |
| 5,383,874 A | 1/1995 | Jackson et al. | 606/1 |
| 5,383,876 A | 1/1995 | Nardella | 606/49 |
| 5,383,917 A | 1/1995 | Desai et al. | 607/702 |
| 5,389,096 A | 2/1995 | Aita | 606/15 |
| 5,395,312 A | 3/1995 | Desai | 604/22 |
| 5,400,267 A | 3/1995 | Denen et al. | 702/59 |
| 5,401,272 A | 3/1995 | Perkins | 606/15 |
| 5,403,311 A | 4/1995 | Abele et al. | 606/49 |
| 5,417,687 A | 5/1995 | Nardella et al. | 606/32 |
| 5,419,767 A | 5/1995 | Eggers et al. | 604/114 |
| 5,423,810 A | 6/1995 | Goble et al. | 606/40 |
| 5,423,882 A | 6/1995 | Jackman et al. | 607/122 |
| 5,436,566 A | 7/1995 | Thompson et al. | 324/713 |
| 5,437,662 A | 8/1995 | Nardella | 606/40 |
| 5,438,302 A | 8/1995 | Goble | 331/167 |
| 5,441,499 A | 8/1995 | Fritzsch | 606/45 |

(56) References Cited

U.S. PATENT DOCUMENTS

| | | | |
|---|---|---|---|
| 5,449,356 A | 9/1995 | Walbrink et al. | 606/49 |
| 5,451,224 A | 9/1995 | Goble et al. | 606/48 |
| 5,454,809 A | 10/1995 | Janssen | 606/41 |
| 5,458,596 A | 10/1995 | Lax et al. | 606/31 |
| 5,458,597 A | 10/1995 | Edwards et al. | 606/41 |
| 5,472,443 A | 12/1995 | Cordis et al. | 606/48 |
| 5,486,161 A | 1/1996 | Lax et al. | 604/22 |
| 5,496,312 A | 3/1996 | Klicek | 606/34 |
| 5,496,314 A | 3/1996 | Eggers | 606/41 |
| 5,496,317 A | 3/1996 | Goble et al. | 606/48 |
| 5,505,730 A | 4/1996 | Edwards | 606/41 |
| 5,507,743 A | 4/1996 | Edwards et al. | 606/41 |
| 5,514,130 A | 5/1996 | Baker | 606/41 |
| 5,540,683 A | 7/1996 | Ichikawa et al. | 606/40 |
| 5,542,915 A | 8/1996 | Edwards et al. | 604/22 |
| 5,549,598 A | 8/1996 | O'Donnell, Jr. | 606/6 |
| 5,554,152 A | 9/1996 | Aita | 606/7 |
| 5,556,397 A | 9/1996 | Long et al. | 606/48 |
| 5,562,703 A | 10/1996 | Desai | 606/210 |
| 5,569,242 A | 10/1996 | Lax et al. | 606/42 |
| 5,571,100 A | 11/1996 | Goble et al. | 606/41 |
| 5,573,533 A | 11/1996 | Strul | 606/34 |
| 5,584,872 A | 12/1996 | LaFontaine et al. | 607/117 |
| 5,588,960 A | 12/1996 | Edwards et al. | 604/20 |
| 5,599,350 A | 2/1997 | Schulze et al. | 606/51 |
| 5,609,151 A | 3/1997 | Mulier et al. | 128/642 |
| 5,633,578 A | 5/1997 | Eggers et al. | 323/301 |
| 5,634,921 A | 6/1997 | Hood et al. | 606/5 |
| 5,643,304 A | 7/1997 | Schechter et al. | 606/171 |
| 5,647,869 A | 7/1997 | Goble et al. | 606/37 |
| 5,658,278 A | 8/1997 | Imran et al. | 606/41 |
| 5,660,567 A | 8/1997 | Nierlich et al. | 439/620.21 |
| 5,662,680 A | 9/1997 | Desai | 606/210 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,697,927 A | 12/1997 | Imran et al. | 606/41 |
| 5,700,262 A | 12/1997 | Acosta et al. | 606/48 |
| 5,715,817 A | 2/1998 | Stevens-Wright et al. | 600/373 |
| 5,722,975 A | 3/1998 | Edwards et al. | 606/41 |
| 5,725,524 A | 3/1998 | Mulier et al. | 606/41 |
| 5,749,869 A | 5/1998 | Lindenmeier et al. | 606/34 |
| 5,749,871 A | 5/1998 | Hood et al. | 606/50 |
| 5,749,914 A | 5/1998 | Janssen | 607/116 |
| 5,755,753 A | 5/1998 | Knowlton | 607/98 |
| 5,766,153 A | 6/1998 | Eggers et al. | 604/114 |
| 5,769,847 A | 6/1998 | Panescu et al. | 606/42 |
| 5,785,705 A | 7/1998 | Baker | 606/32 |
| 5,786,578 A | 7/1998 | Christy et al. | 219/720 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,802 A | 9/1998 | Panescu et al. | 606/31 |
| 5,810,809 A | 9/1998 | Rydell | 606/49 |
| 5,836,875 A | 11/1998 | Webster, Jr. | 600/374 |
| 5,836,897 A | 11/1998 | Sakurai et al. | 601/2 |
| 5,843,019 A | 12/1998 | Eggers et al. | 604/22 |
| 5,860,951 A | 1/1999 | Eggers | 604/510 |
| 5,860,974 A | 1/1999 | Abele | 606/41 |
| 5,860,975 A | 1/1999 | Goble et al. | 606/45 |
| 5,871,469 A | 2/1999 | Eggers et al. | 604/114 |
| 5,873,855 A | 2/1999 | Eggers et al. | 604/114 |
| 5,873,877 A | 2/1999 | McGaffigan | 606/41 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier et al. | 606/41 |
| 5,902,272 A | 5/1999 | Eggers et al. | 604/114 |
| 5,944,715 A | 8/1999 | Goble et al. | 606/41 |
| 5,954,716 A | 9/1999 | Sharkey et al. | 606/32 |
| 5,964,786 A | 10/1999 | Ochs et al. | 607/5 |
| 6,004,319 A | 12/1999 | Goble et al. | 606/48 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,027,501 A | 2/2000 | Goble et al. | 606/41 |
| 6,039,734 A | 3/2000 | Goble et al. | 606/41 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,489 A | 5/2000 | Fields et al. | 435/236 |
| 6,068,628 A | 5/2000 | Fanton et al. | 606/41 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,090,107 A | 7/2000 | Borgmeier et al. | 606/41 |
| 6,093,186 A | 7/2000 | Goble | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,135,999 A | 10/2000 | Fanton et al. | 606/45 |
| 6,142,992 A | 11/2000 | Cheng et al. | 606/34 |
| 6,149,620 A | 11/2000 | Baker et al. | 604/22 |
| 6,156,334 A | 12/2000 | Meyer-ingold et al. | 424/443 |
| 6,159,194 A | 12/2000 | Eggers et al. | 604/500 |
| 6,159,208 A | 12/2000 | Hovda et al. | 606/41 |
| 6,162,217 A | 12/2000 | Kannenberg et al. | 606/34 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,197,021 B1 | 3/2001 | Panescu et al. | 606/31 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Goble et al. | 128/898 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,238,393 B1 | 5/2001 | Mulier et al. | 606/41 |
| 6,241,723 B1 | 6/2001 | Heim et al. | 606/34 |
| 6,249,706 B1 | 6/2001 | Sobota et al. | 607/115 |
| 6,254,600 B1 | 7/2001 | Willink et al. | 606/41 |
| 6,258,087 B1 | 7/2001 | Edwards et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 604/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Ruhr et al. | 600/338 |
| 6,309,387 B1 | 10/2001 | Eggers et al. | 606/41 |
| 6,312,408 B1 | 11/2001 | Eggers et al. | 604/114 |
| 6,319,007 B1 | 11/2001 | Livaditis | 433/224 |
| 6,322,549 B1 | 11/2001 | Eggers et al. | 604/500 |
| 6,346,104 B2 | 2/2002 | Daly et al. | 606/34 |
| 6,346,107 B1 | 2/2002 | Cucin | 606/49 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,351 B1 | 4/2002 | Thapliyal et al. | 606/41 |
| 6,391,025 B1 | 5/2002 | Weinstein et al. | 606/41 |
| 6,409,722 B1 | 6/2002 | Hoey et al. | 606/34 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |

(56) References Cited

U.S. PATENT DOCUMENTS

| | | |
|---|---|---|
| 6,425,912 B1 | 7/2002 | Knowlton .................. 607/101 |
| 6,432,103 B1 | 8/2002 | Ellsberry et al. ............. 606/41 |
| 6,440,129 B1 | 8/2002 | Simpson ..................... 606/42 |
| 6,468,274 B1 | 10/2002 | Alleyne et al. ............... 606/32 |
| 6,468,275 B1 | 10/2002 | Wampler et al. .............. 606/48 |
| 6,482,201 B1 | 11/2002 | Olsen et al. .................. 606/41 |
| 6,514,248 B1 | 2/2003 | Eggers et al. ................. 606/41 |
| 6,514,250 B1 | 2/2003 | Jahns et al. .................. 606/41 |
| 6,517,498 B1 | 2/2003 | Burbank et al. ............. 600/564 |
| 6,530,922 B2 | 3/2003 | Cosman ...................... 606/34 |
| 6,558,382 B2 | 5/2003 | Jahns et al. .................. 606/41 |
| 6,565,560 B1 | 5/2003 | Goble et al. .................. 606/41 |
| 6,578,579 B2 | 6/2003 | Burnside .................... 128/897 |
| 6,589,237 B2 | 7/2003 | Woloszko et al. ............. 606/41 |
| 6,602,248 B1 | 8/2003 | Sharps et al. ................. 606/32 |
| 6,620,156 B1 | 9/2003 | Garito et al. ................. 606/50 |
| 6,632,193 B1 | 10/2003 | Davison et al. ............... 604/22 |
| 6,632,220 B1 | 10/2003 | Eggers et al. ................. 606/41 |
| 6,635,034 B1 | 10/2003 | Cosmescu .................. 604/289 |
| 6,640,128 B2 | 10/2003 | Vilsmeier et al. ............ 600/427 |
| 6,656,177 B2 | 12/2003 | Truckai et al. ................ 606/51 |
| 6,663,554 B1 | 12/2003 | Babaev ......................... 600/2 |
| 6,663,627 B2 | 12/2003 | Francischelli et al. ......... 606/41 |
| 6,702,810 B2 | 3/2004 | McClurken et al. ............ 606/34 |
| 6,730,080 B2 | 5/2004 | Harano et al. ................ 606/38 |
| 6,746,447 B2 | 6/2004 | Davison et al. ............... 606/41 |
| 6,749,604 B1 | 6/2004 | Eggers et al. ................. 606/41 |
| 6,749,608 B2 | 6/2004 | Garito et al. ................. 606/45 |
| D493,530 S | 7/2004 | Reschke .................... D24/144 |
| 6,770,071 B2 | 8/2004 | Woloszko et al. ............. 606/41 |
| 6,780,178 B2 | 8/2004 | Palanker et al. .............. 600/41 |
| 6,780,180 B1 | 8/2004 | Goble et al. .................. 606/41 |
| 6,780,184 B2 | 8/2004 | Tanrisever ................... 606/45 |
| 6,802,842 B2 | 10/2004 | Ellman et al. ................. 606/45 |
| 6,837,887 B2 | 1/2005 | Woloszko et al. ............. 606/41 |
| 6,837,888 B2 | 1/2005 | Ciarrocca et al. ............. 606/41 |
| 6,864,686 B2 | 3/2005 | Novak et al. ................. 324/419 |
| 6,866,671 B2 | 3/2005 | Tierney et al. .............. 606/130 |
| 6,872,183 B2 | 3/2005 | Sampson et al. ............. 600/561 |
| 6,878,149 B2 | 4/2005 | Gatto ......................... 606/46 |
| 6,890,307 B2 | 5/2005 | Kokate et al. ............... 600/549 |
| 6,892,086 B2 | 5/2005 | Russell ....................... 600/372 |
| 6,911,027 B1 | 6/2005 | Edwards et al. ............... 606/40 |
| 6,920,883 B2 | 7/2005 | Bessette et al. .............. 128/898 |
| 6,921,398 B2 | 7/2005 | Carmel et al. ................ 606/41 |
| 6,929,640 B1 | 8/2005 | Underwood et al. ............ 606/32 |
| 6,949,096 B2 | 9/2005 | Davison et al. ............... 606/41 |
| 6,953,461 B2 | 10/2005 | McClurken et al. ............ 606/51 |
| 6,960,204 B2 | 11/2005 | Eggers et al. ................. 606/32 |
| 6,974,453 B2 | 12/2005 | Woloszko et al. ............. 606/41 |
| 6,979,328 B2 | 12/2005 | Baerveldt et al. ............... 606/6 |
| 6,979,601 B2 | 12/2005 | Marr et al. .................. 438/132 |
| 6,984,231 B2 | 1/2006 | Goble et al. .................. 606/37 |
| 6,986,770 B2 | 1/2006 | Hood .......................... 606/41 |
| 6,991,631 B2 | 1/2006 | Woloszko et al. ............. 606/41 |
| 7,001,382 B2 | 2/2006 | Gallo .......................... 606/41 |
| 7,004,941 B2 | 2/2006 | Tvinnereim et al. ........... 606/41 |
| 7,010,353 B2 | 3/2006 | Gan et al. .................... 607/50 |
| 7,041,102 B2 | 5/2006 | Truckai et al. ................ 606/51 |
| 7,070,596 B1 | 7/2006 | Woloszko et al. ............. 606/41 |
| 7,090,672 B2 | 8/2006 | Underwood et al. ............ 606/41 |
| 7,094,215 B2 | 8/2006 | Davison et al. ............... 604/22 |
| 7,094,231 B1 | 8/2006 | Ellman et al. ................. 606/37 |
| 7,104,986 B2 | 9/2006 | Hovda et al. ................. 606/32 |
| 7,115,139 B2 | 10/2006 | McClurken et al. ............ 607/96 |
| 7,131,969 B1 | 11/2006 | Hovda et al. ................. 606/45 |
| 7,169,143 B2 | 1/2007 | Eggers et al. ................. 606/32 |
| 7,179,255 B2 | 2/2007 | Lettice et al. ................. 606/32 |
| 7,186,234 B2 | 3/2007 | Dahla et al. .................. 604/22 |
| 7,192,428 B2 | 3/2007 | Eggers et al. ................. 606/41 |
| 7,201,750 B1 | 4/2007 | Eggers et al. ................. 606/41 |
| 7,217,268 B2 | 5/2007 | Eggers et al. ................. 606/32 |
| 7,223,265 B2 | 5/2007 | Keppel ....................... 606/41 |
| 7,241,293 B2 | 7/2007 | Davison ..................... 600/410 |
| 7,247,155 B2 | 7/2007 | Hoey et al. ................... 606/34 |
| 7,270,658 B2 | 9/2007 | Woloszko et al. ............. 606/32 |
| 7,270,659 B2 | 9/2007 | Ricart et al. .................. 606/32 |
| 7,270,661 B2 | 9/2007 | Dahla et al. .................. 606/41 |
| 7,271,363 B2 | 9/2007 | Lee et al. ................. 219/121.43 |
| 7,276,061 B2 | 10/2007 | Schaer et al. ................. 607/41 |
| 7,276,063 B2 | 10/2007 | Davison et al. ............... 606/45 |
| 7,278,994 B2 | 10/2007 | Goble .......................... 606/41 |
| 7,282,048 B2 | 10/2007 | Goble et al. .................. 606/34 |
| 7,297,143 B2 | 11/2007 | Woloszko et al. ............. 606/41 |
| 7,297,145 B2 | 11/2007 | Woloszko et al. ............. 606/41 |
| 7,318,823 B2 | 1/2008 | Sharps et al. ................. 606/32 |
| 7,331,956 B2 | 2/2008 | Hovda et al. ................. 606/32 |
| 7,335,199 B2 | 2/2008 | Goble et al. .................. 606/41 |
| RE40,156 E | 3/2008 | Sharps et al. ................. 606/32 |
| 7,344,532 B2 | 3/2008 | Goble et al. .................. 606/34 |
| 7,357,798 B2 | 4/2008 | Sharps et al. ................. 606/32 |
| 7,387,625 B2 | 6/2008 | Hovda et al. ................. 606/32 |
| 7,419,488 B2 | 9/2008 | Ciarrocca et al. ............. 606/41 |
| 7,429,260 B2 | 9/2008 | Underwood et al. ............ 606/32 |
| 7,429,262 B2 | 9/2008 | Woloszko et al. ............. 606/46 |
| 7,435,247 B2 | 10/2008 | Woloszko et al. ............. 604/45 |
| 7,442,191 B2 | 10/2008 | Hovda et al. ................. 606/41 |
| 7,445,618 B2 | 11/2008 | Eggers et al. ................. 604/48 |
| 7,449,021 B2 | 11/2008 | Underwood et al. ............ 606/32 |
| 7,462,178 B2 | 12/2008 | Woloszko et al. ............ 607/105 |
| 7,468,059 B2 | 12/2008 | Eggers et al. ................. 606/32 |
| 7,491,200 B2 | 2/2009 | Underwood et al. ............ 606/32 |
| 7,507,236 B2 | 3/2009 | Eggers et al. ................. 606/41 |
| 7,527,624 B2 | 5/2009 | Dubnack et al. .............. 606/41 |
| 7,572,251 B1 | 8/2009 | Davison et al. .............. 604/500 |
| 7,632,267 B2 | 12/2009 | Dahla ......................... 606/41 |
| 7,678,069 B1 | 3/2010 | Baker et al. .................. 604/22 |
| 7,691,101 B2 | 4/2010 | Davison et al. ............... 606/41 |
| 7,699,830 B2 | 4/2010 | Martin ....................... 604/540 |
| 7,704,249 B2 | 4/2010 | Woloszko et al. ............. 606/48 |
| 7,708,733 B2 | 5/2010 | Sanders et al. ............... 606/41 |
| 7,722,601 B2 | 5/2010 | Wham et al. ................. 606/34 |
| 7,785,322 B2 | 8/2010 | Penny et al. .................. 606/34 |
| 7,824,398 B2 | 11/2010 | Woloszko et al. ............. 606/45 |
| 7,862,560 B2 | 1/2011 | Marion ....................... 606/34 |
| 7,879,034 B2 | 2/2011 | Woloszko et al. ............. 606/48 |
| 7,892,230 B2 | 2/2011 | Woloszko et al. ............. 606/41 |
| 7,901,403 B2 | 3/2011 | Woloszko et al. ............. 606/48 |
| 7,985,072 B2 | 7/2011 | Belikov et al. ............... 433/215 |
| 7,988,689 B2 | 8/2011 | Woloszko et al. ............. 606/41 |
| 8,012,153 B2 | 9/2011 | Woloszko et al. ............. 606/48 |
| 8,114,071 B2 | 2/2012 | Woloszko et al. ............. 606/32 |
| D658,760 S | 5/2012 | Cox et al. ................... D24/144 |
| 8,192,424 B2 | 6/2012 | Woloszko .................... 606/40 |
| 2002/0029036 A1 | 3/2002 | Goble et al. .................. 606/38 |
| 2002/0042612 A1 | 4/2002 | Hood et al. .................. 606/50 |
| 2002/0151882 A1 | 10/2002 | Marko et al. ................. 606/28 |
| 2002/0183739 A1 | 12/2002 | Long .......................... 606/41 |
| 2003/0013986 A1 | 1/2003 | Saadat ....................... 600/549 |
| 2003/0014045 A1 | 1/2003 | Russell ....................... 606/41 |
| 2003/0014047 A1 | 1/2003 | Woloszko et al. ............. 606/41 |
| 2003/0088245 A1 | 5/2003 | Woloszko et al. ............. 606/41 |
| 2003/0158545 A1 | 8/2003 | Hovda et al. ................. 606/32 |
| 2003/0171743 A1 | 9/2003 | Tasto et al. ................... 606/32 |
| 2003/0181903 A1 | 9/2003 | Hood et al. .................. 606/49 |
| 2003/0208196 A1 | 11/2003 | Stone ......................... 606/41 |
| 2003/0212396 A1 | 11/2003 | Eggers et al. ................. 606/41 |
| 2003/0216725 A1 | 11/2003 | Woloszko et al. ............. 606/41 |
| 2003/0216732 A1 | 11/2003 | Truckai et al. ................ 606/49 |
| 2003/0232048 A1 | 12/2003 | Yang et al. ................. 424/141.1 |
| 2004/0030330 A1 | 2/2004 | Brassell et al. ............... 606/41 |
| 2004/0116922 A1 | 6/2004 | Hovda et al. ................. 606/41 |
| 2004/0127893 A1 | 7/2004 | Hovda ....................... 606/41 |
| 2004/0186418 A1 | 9/2004 | Karashima .................. 604/20 |
| 2004/0230190 A1 | 11/2004 | Dahla et al. .................. 604/41 |
| 2005/0004634 A1 | 1/2005 | Ricart et al. .................. 606/41 |
| 2005/0033278 A1 | 2/2005 | McClurken et al. ............ 606/34 |
| 2005/0197657 A1* | 9/2005 | Goth et al. .................. 606/41 |
| 2005/0245923 A1 | 11/2005 | Christopherson et al. ...... 606/41 |
| 2005/0261754 A1 | 11/2005 | Woloszko et al. ............. 606/32 |
| 2005/0273091 A1 | 12/2005 | Booth et al. .................. 607/99 |
| 2006/0036237 A1 | 2/2006 | Davison et al. ............... 606/41 |
| 2006/0095031 A1 | 5/2006 | Ormsby ....................... 606/34 |
| 2006/0161148 A1 | 7/2006 | Behnke ....................... 606/34 |

(56) References Cited

U.S. PATENT DOCUMENTS

| | | | |
|---|---|---|---|
| 2006/0189971 A1 | 8/2006 | Tasto et al. | 606/32 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2008/0077128 A1 | 3/2008 | Woloszko et al. | 606/41 |
| 2008/0138761 A1 | 6/2008 | Pond | 433/29 |
| 2008/0154255 A1 | 6/2008 | Panos et al. | 606/33 |
| 2008/0243116 A1 | 10/2008 | Anderson | 606/41 |
| 2008/0300590 A1 | 12/2008 | Horne et al. | 606/35 |
| 2009/0209956 A1 | 8/2009 | Marion | 606/34 |
| 2009/0222001 A1 | 9/2009 | Greeley | 606/33 |
| 2010/0152726 A1 | 6/2010 | Cadouri et al. | 606/41 |
| 2010/0228246 A1 | 9/2010 | Marion | 606/37 |
| 2010/0292689 A1 | 11/2010 | Davison et al. | 606/41 |
| 2010/0318083 A1 | 12/2010 | Davison et al. | 606/41 |
| 2010/0324549 A1 | 12/2010 | Marion | 606/37 |
| 2011/0137308 A1 | 6/2011 | Woloszko et al. | 606/41 |
| 2011/0245826 A1 | 10/2011 | Woloszko et al. | 606/41 |
| 2012/0083782 A1 | 4/2012 | Stalder et al. | 606/41 |
| 2012/0095453 A1 | 4/2012 | Cox et al. | 606/33 |
| 2012/0095454 A1 | 4/2012 | Cox et al. | 606/33 |
| 2012/0109123 A1 | 5/2012 | Woloszko et al. | 606/45 |
| 2012/0196251 A1 | 8/2012 | Taft et al. | 433/216 |
| 2012/0197344 A1 | 8/2012 | Taft et al. | 607/51 |

FOREIGN PATENT DOCUMENTS

| | | | |
|---|---|---|---|
| EP | 423757 | 3/1996 | A61B 17/39 |
| EP | 0703461 A2 | 3/1996 | G01B 27/02 |
| EP | 0740926 A2 | 11/1996 | A61B 17/36 |
| EP | 0754437 A2 | 1/1997 | A61B 17/39 |
| EP | 0694290 B1 | 11/2000 | A61B 18/04 |
| EP | 1334699 | 8/2003 | A61B 18/12 |
| EP | 1428480 | 6/2004 | A61B 18/12 |
| EP | 1707147 | 10/2006 | A61B 18/12 |
| FR | 2313949 | 1/1977 | A61N 3/02 |
| GB | 467502 | 6/1937 | |
| GB | 2160102 | 12/1985 | A61B 17/38 |
| GB | 2299216 | 9/1996 | H01F 30/12 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| GB | 2333455 | 7/1999 | G01K 11/12 |
| GB | 2406793 | 4/2005 | A61B 18/00 |
| JP | 57-57802 | 4/1982 | A61B 1/00 |
| JP | 57-117843 | 7/1982 | A61B 17/39 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | A61N 1/06 |
| WO | 94/08654 | 4/1994 | A61M 37/00 |
| WO | 94/10921 | 5/1994 | A61B 18/00 |
| WO | 94/26228 | 11/1994 | A61B 18/14 |
| WO | 95/34259 | 12/1995 | A61F 5/48 |
| WO | 96/00040 | 1/1996 | A61B 18/00 |
| WO | 96/00042 | 1/1996 | A61B 17/39 |
| WO | 96/39086 | 12/1996 | A61B 18/12 |
| WO | 97/00646 | 1/1997 | A61B 17/39 |
| WO | 97/00647 | 1/1997 | A61B 17/39 |
| WO | 97/18768 | 5/1997 | A61B 17/39 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/43971 | 11/1997 | A61B 17/39 |
| WO | 97/48345 | 12/1997 | A61B 17/39 |
| WO | 97/48346 | 12/1997 | A61B 17/39 |
| WO | 98/07468 | 2/1998 | A61N 1/40 |
| WO | 98/26724 | 6/1998 | A61B 17/36 |
| WO | 98/27879 | 7/1998 | A61B 17/36 |
| WO | 98/27880 | 7/1998 | A61B 17/39 |
| WO | 98/56324 | 12/1998 | A61F 7/12 |
| WO | 99/20213 | 4/1999 | A61F 7/12 |
| WO | 99/51155 | 10/1999 | A61B 17/36 |
| WO | 99/51158 | 10/1999 | A61B 17/39 |
| WO | 99/56648 | 11/1999 | A61B 17/39 |
| WO | 00/00098 | 1/2000 | A61B 17/36 |
| WO | 00/09053 | 2/2000 | A61F 7/12 |
| WO | 01/24720 | 4/2001 | A61B 18/18 |
| WO | 01/87154 | 5/2001 | A61B 5/05 |
| WO | 01/95819 | 12/2001 | A61B 18/14 |
| WO | 02/36028 | 5/2002 | A61B 18/12 |
| WO | 02/102255 | 12/2002 | A61B 17/20 |
| WO | 03/024305 | 3/2003 | |
| WO | 03/092477 | 11/2003 | |
| WO | 2004/026150 | 4/2004 | A61B 17/22 |
| WO | 2004/071278 | 8/2004 | |
| WO | 2005/125287 | 12/2005 | A61B 18/00 |
| WO | 2007/006000 | 1/2007 | A61B 18/14 |
| WO | 2007/056729 | 5/2007 | A61B 18/14 |
| WO | 2010/052717 | 5/2010 | A61B 18/14 |
| WO | 2012/050636 | 4/2012 | A61B 18/14 |
| WO | 2012/050637 | 4/2012 | A61B 18/14 |

OTHER PUBLICATIONS

BiLAP Generator Settings, Jun. 1991.

BiLAP IFU 910026-001 Rev A for BiLAP Model 3525, J-Hook, 4 pgs, May 20, 1991.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

Codman & Shurtleff, Inc. "The Malis Bipolar Coagulating and Bipolar Cutting System CMC-II" brochure, early, 2 pgs, 1991.

Codman & Shurtleff, Inc. "The Malis Bipolar Electrosurgical System CMC—III Instruction Manual", 15 pgs, Jul. 1991.

Cook et al., "Therapeutic Medical Devices: Application and Design", Prentice Hall, Inc., 3pgs 1982.

Dennis et al. "Evolution of Electrofulguration in Control of Bleeding of Experimental Gastric Ulcers," Digestive Diseases and Sciences, vol. 24, No. 11, 845-848, Nov. 1979.

Dobbie, A.K., "The Electrical Aspects of Surgical Diathermy, Bio Medical Engineering" *Bio-Medical Engineering* vol. 4, pp. 206-216, May 1969.

Elsasser, V.E. et al., "An Instrument for Transurethral Resection without Leakage of Current" *Acta Medicotechnica* vol. 24, No. 4, pp. 129-134, 1976.

Geddes, "Medical Device Accidents: With Illustrative Cases" CRC Press, 3 pgs, 1998.

Honig, W., "The Mechanism of Cutting in Electrosurgery" *IEEE* pp. 58-65, 1975.

Kramolowsky et al. "The Urological App of Electorsurgery" J. of Urology vol. 146, pp. 669-674 1991.

Kramolowsky et al. "Use of 5F Bipolar Electrosurgical Probe in Endoscopic Urological Procedures" *J. of Urology* vol. 143, pp. 275-277, 1990.

Lee, B et al. "Thermal Compression and Molding of Artheroslerotic Vascular Tissue with Use" JACC vol. 13(5), pp. 1167-1171, 1989.

Letter from Department of Health to Jerry Malis dated Jan. 24, 1991, 3 pgs.

Letter from Department of Health to Jerry Malis dated Jul. 25, 1985, 1 pg.

Letter from Jerry Malis to FDA dated Jul. 25, 1985, 2 pgs.

Lu, et al., "Electrical Thermal Angioplasty: Catheter Design Features, In Vitro Tissue Ablation Studies and In Vitro Experimental Findings," *Am J. Cardiol* vol. 60, pp. 1117-1122, Nov. 1, 1987.

Malis, L., "Electrosurgery, Technical Note," *J. Neursurg.*, vol. 85, pp. 970-975, Nov. 1996.

Malis, L., "Excerpted from a seminar by Leonard I. Malis, M.D. at the 1995 American Association of Neurological Surgeons Meeting," 1pg, 1995.

(56) References Cited

OTHER PUBLICATIONS

Malis, L., "Instrumentation for Microvascular Neurosurgery" *Cerebrovascular Surgery*, vol. 1, pp. 245-260, 1985.
Malis, L., "New Trends in Microsurgery and Applied Technology," *Advanced Technology in Neurosurgery*, pp. 1-16, 1988.
Malis, L., "The Value of Irrigation During Bipolar Coagulation" See ARTC 21602, 1 pg, Apr. 9, 1993.
Nardella, P.C., *SPIE* 1068: pp. 42-49, Radio Frequency Energy and Impedance Feedback, 1989.
O'Malley, Schaum's Outline of Theory and Problems of Basic Circuit Analysis, McGraw-Hill, $2^{nd}$ Ed., pp. 3-5, 1992.
Olsen MD, Bipolar Laparoscopic Cholecstectomy Lecture (marked confidential), 12 pgs, Oct. 7, 1991.
Pearce, John A. "Electrosurgery", pp. 17, 69-75, 87, John Wiley & Sons, New York, 1986.
Pearce, John A., "Electrosurgery", Handbook of Biomedical Engineering, chapter 3, Academic Press Inc., N.Y., pp. 98-113, 1988.
Piercey et al., "Electrosurgical Treatment of Experimental Bleeding Canine Gastric Ulcers" *Gastroenterology* vol. 74(3), pp. 527-534, 1978.
Protell et al., "Computer-Assisted Electrocoagulation: Bipolar v. Monopolar in the Treatment of Experimental Canine Gastric Ulcer Bleeding," *Gastroenterology* vol. 80, No. 3, pp. 451-455, 1981.
Ramsey et al., "A Comparison of Bipolar and Monopolar Diathermy Probes in Experimental Animals", *Urological Research* vol. 13, pp. 99-102, 1985.
Selikowitz et al., "Electric Current and Voltage Recordings on the Myocardium During Electrosurgical Procedures in Canines," *Surgery, Gynecology & Obstetrics*, vol. 164, pp. 219-224, Mar. 1987.
Shuman, "Bipolar Versus Monopolar Electrosurgery: Clinical Applications," *Dentistry Today*, vol. 20, No. 12, 7 pgs, Dec. 2001.
Slager et al. "Spark Erosion of Arteriosclerotic Plaques" *Z. Kardiol.* 76:Suppl. 6, pp. 67-71, 1987.
Slager et al. "Vaporization of Atherosclerotice Plaques by Spark Erosion" *JACC* 5(6): pp. 1382-1386, Jun. 1985.
Stoffels, E. et al., "Investigation on the Interaction Plasma-Bone Tissue", E-MRS Spring Meeting, 1 pg, Jun. 18-21, 2002.
Stoffels, E. et al., "Biomedical Applications of Plasmas", Tutorial presented prior to the $55^{th}$ Gaseous Electronics Conference in Minneapolis, MN, 41 pgs, Oct. 14, 2002.
Stoffels, E. et al., "Plasma Interactions with Living Cells", Eindhoven University of Technology, 1 pg, 2002.
Stoffels, E. et al., "Superficial Treatment of Mammalian Cells using Plasma Needle", J. Phys. D: Appl. Phys. 26, pp. 2908-2913, Nov. 19, 2003.
Stoffels, E. et al., "Plasma Needle", Eindhoven University of Technology, 1 pg, Nov. 28, 2003.
Stoffels, E. et al., "Plasma Physicists Move into Medicine", Physicsweb, 1 pg, Nov. 2003.
Stoffels, E. et al., "Plasma Treated Tissue Engineered Skin to Study Skin Damage", Biomechanics and Tissue Engineering, Materials Technology, 1 pg, 2003.
Stoffels, E. et al., "Plasma Treatment of Dental Cavities: A Feasibility Study", IEEE Transaction on Plasma Science, vol. 32, No. 4, pp. 1540-1542, Aug. 2004.
Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.
Stoffels, E. et al., "Electrical and Optical Characterization of the Plasma Needle", New Journal of Physics 6, pp. 1-14, Oct. 28, 2004.
Stoffels, E. et al., "Where Plasma Meets Plasma", Eindhoven University of Technology, 23 pgs, 2004.
Stoffels, E. et al., "Gas Plasma effects on Living Cells", Physica Scripta, T107, pp. 79-82, 2004.
Stoffels, E. et al., "Plasma Treatment of Mammalian Vascular Cells: A Quantitative Description", IEEE Transaction on Plasma Science, vol. 33, No. 2, pp. 771-775, Apr. 2005.
Stoffels, E. et al., "Deactivation of *Escherichia coli* by the Plasma Needle", J. Phys. D: Appl. Phys. 38, pp. 1716-1721, May 20, 2005.
Stoffels, E. et al., "Development of a Gas Plasma Catheter for Gas Plasma Surgery", XXVIIth ICPIG, Endoven University of Technology, pp. 18-22, Jul. 2005.
Stoffels, E. et al., "Development of a Smart Positioning Sensor for the Plasma Needle", Plasma Sources Sci. Technol. 15, pp. 582-589, Jun. 27, 2006.
Stoffels, E. et al., Killing of S. Mutans Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and Streptococcus Mutans", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop",Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, CLINICA, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93 1995.
Wyeth, "Electrosurgical Unit" pp. 1181-1202, 2000.
Buchelt, et al. "Excimer Laser Ablation of Fibrocartilage: An In Vitro and In Vivo tudy", Lasers in Surgery and Medicine, vol. 11, pp. 271-279, 1991.
Costello et al., "Nd: YAG Laser Ablation of the Prostate as a Treatment for Benign Prostatic Hypertrophy", Lasers in Surgery and Medicine, vol. 12, pp. 121-124, 1992.
O'Neill et al., "Percutaneous Plasma Discectomy Stimulates Repair in Injured Porcine Intervertebral Discs", Dept. of Orthopaedic Surgery, Dept. of Radiology University of California at San Francisco, CA, 3 pgs No date.
Rand et al., "Effect of Elecctrocautery on Fresh Human Articular Cartilage", J. Arthro. Surg., vol. 1, pp. 242-246, 1985.
European Examination Report for EP 02773432 4 pgs, Sep. 22, 2009.
European Examination Report for EP 05024974 4 pgs, Dec. 5, 2008.
European Examination Report for EP 04708664 7pgs, Sep. 7, 2009.
European Examination Report for EP 02749601.7 4pgs, Dec. 2, 2009.
European Examination Report 2 for EP 04708664 5pgs, May 3, 2010.
European Search Report for EP 02773432 3pgs, Dec. 19, 2008.
European Search Report for EP 04708664.0 5pgs Apr. 6, 2009.
European Search Report for EP 98953859, 2 pgs, Jul. 2, 2001.
Suppl European Search Report for EP 98953859, 3 pgs, Oct. 18, 2001.
Extended European Search Report for EP09152846, 8pgs, Jan. 5, 2010.

(56) References Cited

OTHER PUBLICATIONS

European Search Report for EP 99945039.8, 3 pgs, Oct. 1, 2001.
European Search Report for EP 09152850, 2 pgs, Dec. 29, 2009.
PCT International Preliminary Examination Report for PCT/US02/19261, 3 pgs Mar. 25, 2003.
PCT International Search Report for PCT/US02/19261, 1 pg Mailed Sep. 18, 2002.
PCT International Search Report for PCT/US02/29476, 1 pg Mailed May 24, 2004.
PCT International Search Report for PCT/US03/13686, 1 pg Mailed Nov. 25, 2003.
PCT International Search Report for PCT/US04/03614, 1 pg. Mailed Sep. 14, 2004.
PCT International Search Report for PCT/US98/22323, 1 pg Mailed Mar. 3, 1999.
PCT International Search Report for PCT/US99/14685, 1 pg Mailed Oct. 21, 1999.
PCT International Search Report for PCT/US99/18289, 1 pg. Mailed Dec. 7, 1999.
PCT Notification of International Preliminary Examination Report for PCT/US98/22323, 5 pgs Mailed Nov. 28, 2000.
PCT Notification of International Preliminary Examination Report for PCT/US99/14685, 4 pgs Mailed Feb. 20, 2001.
PCT Notification of International Preliminary Examination Report for PCT/US99/18289 4 pgs Mailed Jul. 7, 2000.
PCT Notification of International Search Report and Written Opinion for PCT/US06/26321, 8pgs Mailed Apr. 25, 2007.
PCT Notification of the International Search Report and Written Opinion for PCT/US06/60618, 7pgs Mailed Oct. 5, 2007.
PCT Notification of the International Search Report and Written Opinion for PCT/US07/69856, 7pgs Mailed Jun. 5, 2008.
PCT Written Opinion of the International Searching Authority for PCT/US04/03614, 4 pgs Mailed Sep. 14, 2004.
PCT Notification of the International Search Report and Written Opinion for PCT/US2011/033784 11 pgs Mailed Jul. 18, 2011.
PCT Notification of the International Search Report and Written Opinion for PCT/US2011/033761 11 pgs Mailed Jul. 22, 2011.
UK Search Report for GB0800129.9 2pgs, May 8, 2008.
UK Search Report for GB0805062.7 1 pg, Jul. 16, 2008.
UK Search Report for GB0900604.0 4 pgs, May 15, 2009.
UK Search Report for GB1110342.1 3pgs, Oct. 18, 2011.

\* cited by examiner

METHOD AND SYSTEM OF AN ELECTROSURGICAL CONTROLLER WITH WAVE-SHAPING

CROSS-REFERENCE TO RELATED APPLICATIONS

This application is a divisional of U.S. application Ser. No. 12/486,013 filed Jun. 17, 2009, the complete disclosure of which is incorporated herein by reference for all purposes.

BACKGROUND

Electrosurgical systems are used by physicians to perform specific functions during surgical procedures. For example, in an ablation mode electrosurgical systems use high frequency electrical energy to remove soft tissue such as sinus tissue, adipose tissue or other tissue such as meniscus, or cartilage or synovial tissue in a joint. In a coagulation mode, the electrosurgical device may aid the surgeon in reducing internal bleeding by assisting in the coagulation and/or sealing of vessels. In both the ablation and coagulation mode, control of the electrical energy to provide a proper ablation and/or coagulation is utilized, and thus any advance that increases the energy control functionality of an electrosurgical system provides competitive advantage.

BRIEF DESCRIPTION OF THE DRAWINGS

For a detailed description of exemplary embodiments, reference will now be made to the accompanying drawings in which.

NOTATION AND NOMENCLATURE

Figure 1:
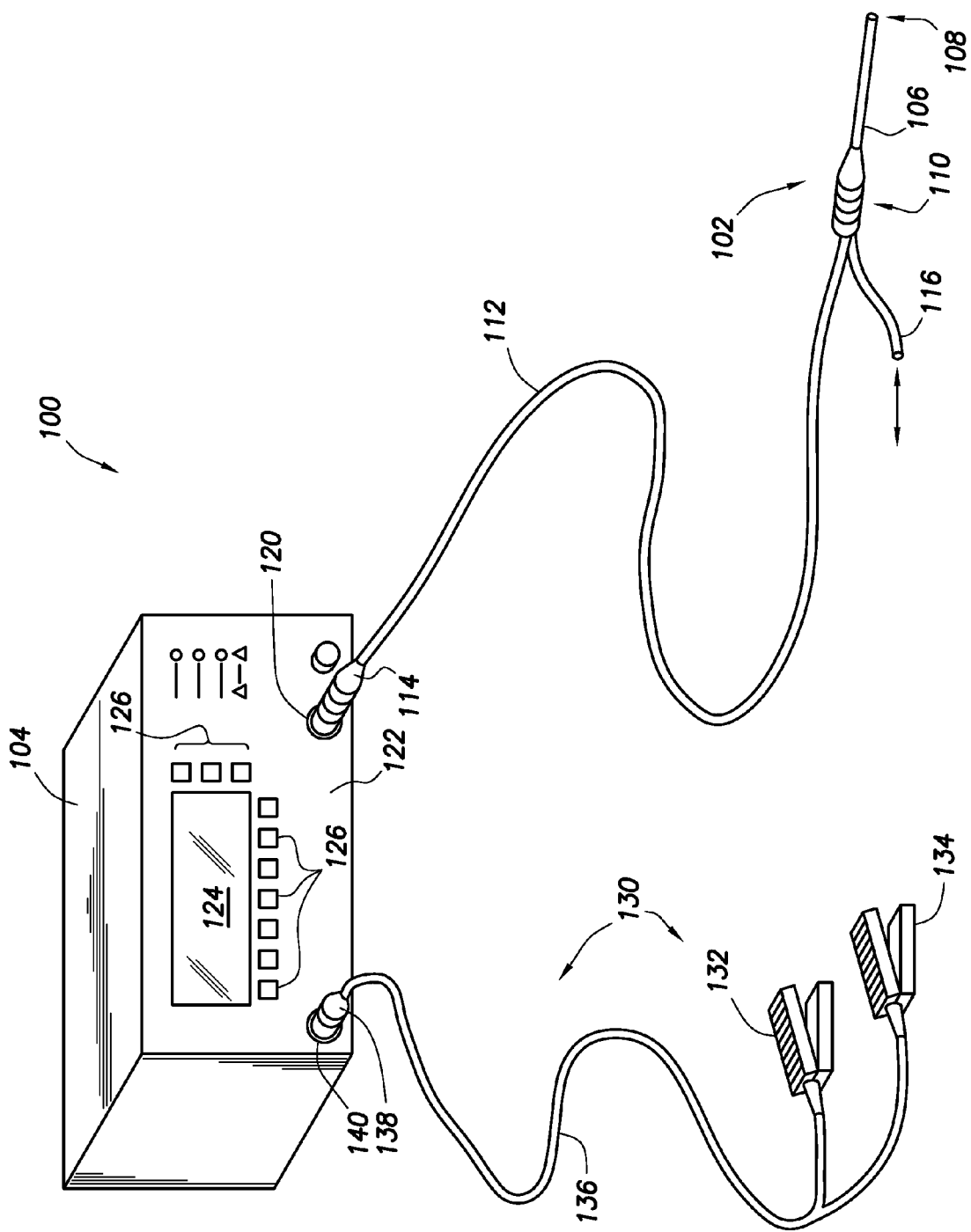
FIG. 1 shows an electrosurgical system in accordance with at least some embodiments.

Certain terms are used throughout the following description and claims to refer to particular system components. As one skilled in the art will appreciate, companies that design and manufacture electrosurgical systems may refer to a component by different names. This document does not intend to distinguish between components that differ in name but not function.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect electrical connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Active electrode" shall mean an electrode of an electrosurgical wand which produces an electrically-induced tissue-altering effect when brought into contact with, or close proximity to, a tissue targeted for treatment, and/or an electrode having a voltage induced thereon by a voltage generator.

"Active terminal" shall mean an electrical connection to a transformer that is configured to couple to an active electrode of an electrosurgical wand.

"Return electrode" shall mean an electrode of an electrosurgical wand which serves to provide a current flow path for electrons with respect to an active electrode, and/or an electrode of an electrosurgical wand which does not itself produce an electrically-induced tissue-altering effect on tissue targeted for treatment.

"Return terminal" shall mean an electrical connection to a transformer that is configured to couple to a return electrode of an electrosurgical wand.

"Center tap", in relation to a transformer, shall mean an electrical connection to a winding of the transformer at approximately the middle turn of the total number of turns; however, the center tap need neither be precisely at the numeric middle nor the physical middle, and a tap that is within 5% of the total number of turns from the numeric middle shall be considered a center tap.

"Fixed", in relation to a direct current (DC) voltage level applied to a winding of a transformer, shall mean a DC voltage level that is either: controlled to a particular DC voltage level during changes in load seen by a secondary of the transformer; or is not adjusted to be a different voltage level in spite of changes in load seen by the secondary of the transformer. The presence of noise (e.g., alternating current (AC) ripple voltages) "riding" the DC voltage level, and drops in voltage caused by current draw of the primary winding, shall not obviate the status of a DC voltage as fixed.

"Different than" in the claims shall mean only that the different devices are individual physical devices. "Different than" shall not be construed to require that the devices are of different construction or configuration. Thus, for example, "a first transformer, different than a second transformer" shall mean that two physical transformers are present, and the two transformers may be of identical physical construction, or different physical construction Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

Before the various embodiments are described in detail, it is to be understood that this invention is not limited to particular variations set forth herein as various changes or modifications may be made, and equivalents may be substituted, without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

FIG. 1 illustrates an electrosurgical system 100 in accordance with at least some embodiments. In particular, the electrosurgical system comprises an electrosurgical wand 102 (hereinafter "wand") coupled to an electrosurgical controller 104 (hereinafter "controller"). In some embodiments the wand 102 comprises an elongated shaft 106 that defines distal end 108 where at least some electrodes are disposed. The elongated shaft 106 further defines a handle or proximal end 110, where a physician grips the wand 102 during surgical procedures. The wand 102 further comprises a flexible multi-conductor cable 112 housing a plurality of electrical leads (not specifically shown in FIG. 1), and the flexible multi-conductor cable 112 terminates in a connector 114. Though not visible in FIG. 1, in some embodiments the wand 102 has an internal passage fluidly coupled to a flexible tubular member 116. The internal passage and flexible tubular member 116 may be used as a conduit to supply conductive fluid to be proximate to the distal end 108, or the internal passage and flexible tubular member may be used to aspirate the area proximate to the distal end 108 of the wand 102. Other wand types may be equivalently used.

The wand 102 couples to the controller 104, such as by a wand connector 120 on an outer surface 122 of the controller 104 (in the illustrative case of FIG. 1 the front surface). A display device or interface panel 124 is visible through the outer surface 122, and in some embodiments a user may select operational modes of the controller 104 by way of the interface panel 124 and related buttons 126. In some embodiments the electrosurgical system 100 also comprises an interface device in the form of a foot pedal assembly 130. The foot pedal assembly 130 may comprise one or more pedal devices 132 and 134, a flexible multi-conductor cable 136 and a connector 138. While only two pedal devices 132, 134 are shown, any number of pedal devices may be implemented. The outer surface 122 of the controller 104 may comprise a corresponding pedal connector 140 that couples to the connector 138. A physician may use the foot pedal assembly 130 to control various aspects of the controller 104. For example, a pedal device, such as pedal device 132, may be used for on-off control of the application of radio frequency (RF) energy to the wand 102. As yet another example, a pedal device, such as pedal device 134, may be used to modify a characteristic of the RF energy delivered to the wand 102, such as by a change in the applied voltage or the shape as a function of time of the voltage of the RF energy.

The electrosurgical system 100 of the various embodiments may have a variety of operational modes. One such mode employs Coblation® technology. In particular, the assignee of the present disclosure is the owner of Coblation® technology. Coblation® technology involves the application of RF energy between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments the electrically conductive fluid is delivered in the vicinity of the active electrodes and/or to the target site by the wand 102, such as by way of the internal passage and flexible tubular member 116.

When the electrically conductive fluid is heated to the point that the atoms of the fluid vaporize faster than the atoms condense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm$^3$ for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. Often, the electrons in the plasma carry the electrical current or absorb the electromagnetic waves and, therefore, are hotter than the ionic particles. Thus, the electrons, which are carried away from the target tissue toward the active or return electrodes, carry most of the plasma's heat, enabling the ionic particles to break apart the target tissue molecules in a substantially non-thermal manner.

By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

In addition to the Coblation® mode, the electrosurgical system 100 of FIG. 1 is also useful for sealing larger arterial vessels (e.g., on the order of about 1 millimeter (mm) in diameter), when used in what is known as a coagulation mode. Thus, the system of FIG. 1 may have an ablation mode where RF energy at a first voltage is applied to one or more active electrodes sufficient to effect molecular dissociation or disintegration of the tissue, and the system of FIG. 1 may also have a coagulation mode where RF energy at a second, lower voltage is applied to one or more active electrodes (either the same or different electrode(s) as the ablation mode) sufficient to heat, shrink, seal, fuse, and/or achieve homeostasis of severed vessels within the tissue.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons.

Figure 2:
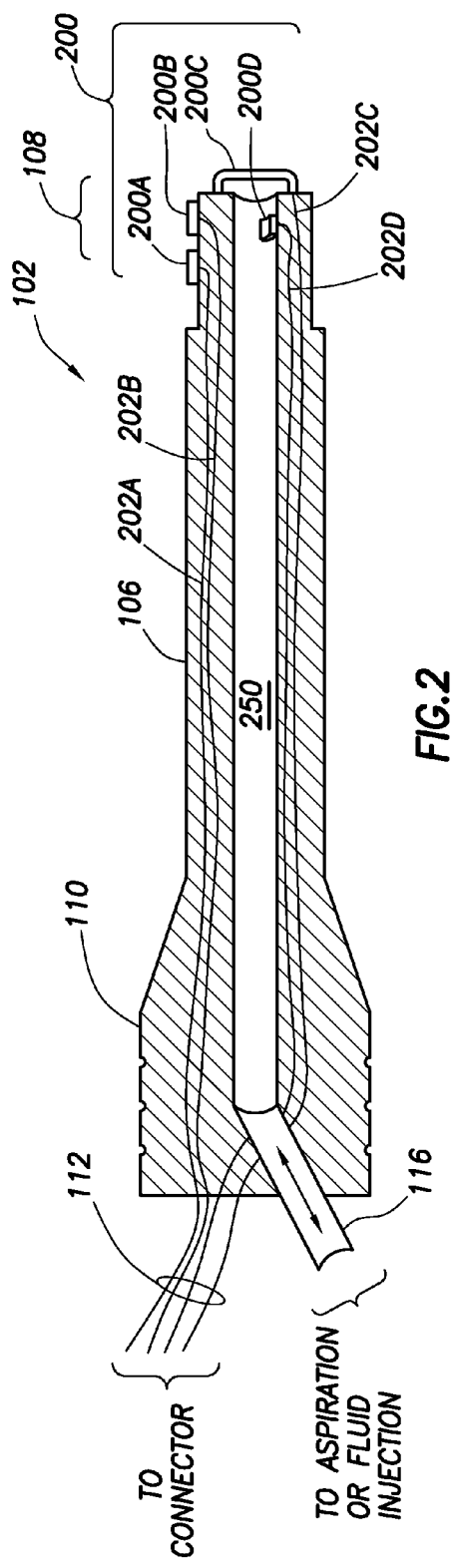
FIG. 2 shows a cross-sectional view of a wand in accordance with at least some embodiments.

FIG. 2 shows a cross-sectional view of wand 102 in accordance with at least some embodiments. In particular, FIG. 2 illustrates the elongated shaft 106 comprising distal end 108 and proximal end 110. Distal end 108 comprises a plurality of electrodes 200. The electrodes of FIG. 2 are merely illustrative, and any arrangement of electrodes may be equivalently used. Each electrode 200 has an electrical lead associated therewith that runs through the elongated shaft 106 to the flexible multi-conductor cable 112. In particular, electrode 200A has dedicated electrical lead 202A which runs within the elongated shaft to the become part of cable 112. Similarly, electrode 200B has dedicated electrical lead 202B which runs within the elongated shaft 106 to become part of cable 112. Illustrative electrodes 200C and 200D likewise have dedicated electrical leads 202C and 202D, respectively, which run within the elongated shaft 106 to become part of cable 112. In some embodiments, the elongated shaft 106 has dedicated internal passages (in addition to optional internal lumen 250) through which the electrical leads 202 run. In other embodiments, the electrical leads 202 are cast within the material that makes up the elongated shaft.

Figure 3:
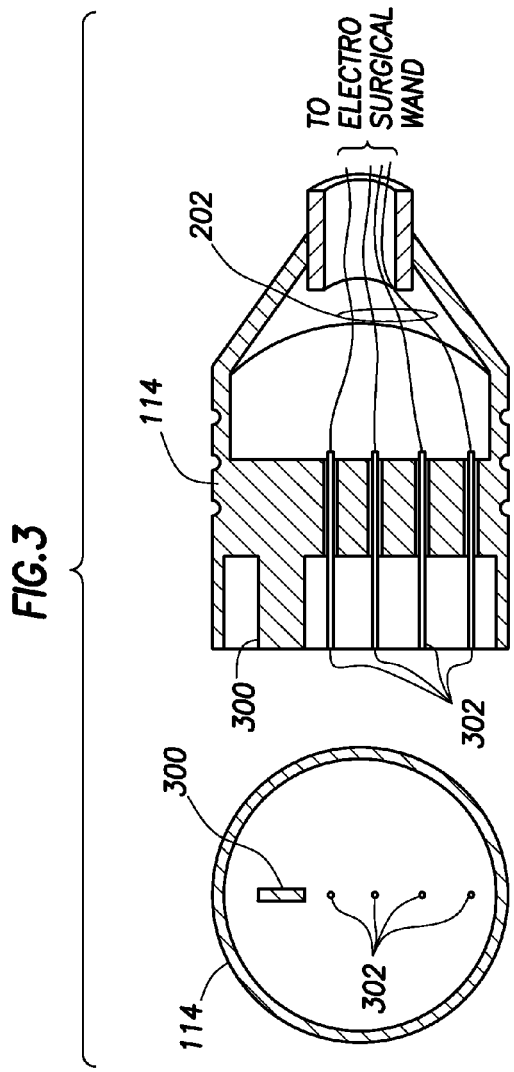
FIG. 3 shows both an elevational end-view (left) and a cross-sectional view (right) of a connector in accordance with at least some embodiments.

As illustrated in FIG. 1, flexible multi-conductor cable 112 (and more particularly its constituent electrical leads 202) couple to the connector 114. Connector 114 couples the controller 104, and more particularly the wand connector 120. FIG. 3 shows both a cross-sectional view (right) and an end elevation view (left) of connector 114 in accordance with at least some embodiments. In particular, connector 114 comprises a tab 300. Tab 300 works in conjunction with a slot on wand connector 120 (shown in FIG. 4) to ensure that the connector 114 and wand connector 120 only couple in one relative orientation. The illustrative connector 114 further comprises a plurality of electrical pins 302 protruding from connector 114. Each electrical pin 302 is coupled to a single electrical lead in the leads 202. While FIG. 3 shows only four illustrative electrical pins, in some embodiments 26 or more electrical pins may be present in the connector 114.

Figure 4:
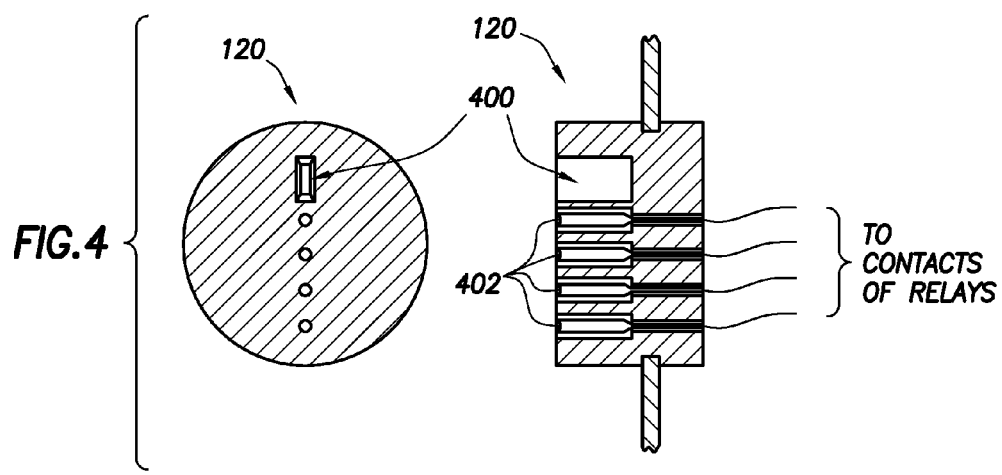
FIG. 4 shows both an elevational end-view (left) and a cross-sectional view (right) of a wand connector in accordance with at least some embodiments.

FIG. 4 shows both a cross-sectional view (right) and an end elevation view (left) of wand connector 120 in accordance with at least some embodiments. In particular, wand connector 120 comprises a slot 400. Slot 400 works in conjunction with a tab 300 on connector 114 (shown in FIG. 3) to ensure that the connector 114 and wand connector 120 only couple in one orientation. The illustrative wand connector 120 further comprises a plurality of electrical pins 402 residing within respective holes of wand connector 120. At least some of the electrical pins 402 are each individually coupled to a voltage generator (discussed more thoroughly below) within the controller 104. When connector 114 and wand connector 120 are coupled, each electrical pin 402 couples to a single electrical pin 302. While FIG. 4 shows only four illustrative electrical pins, in some embodiments 26 or more electrical pins may be present in the wand connector 120.

Figure 5:
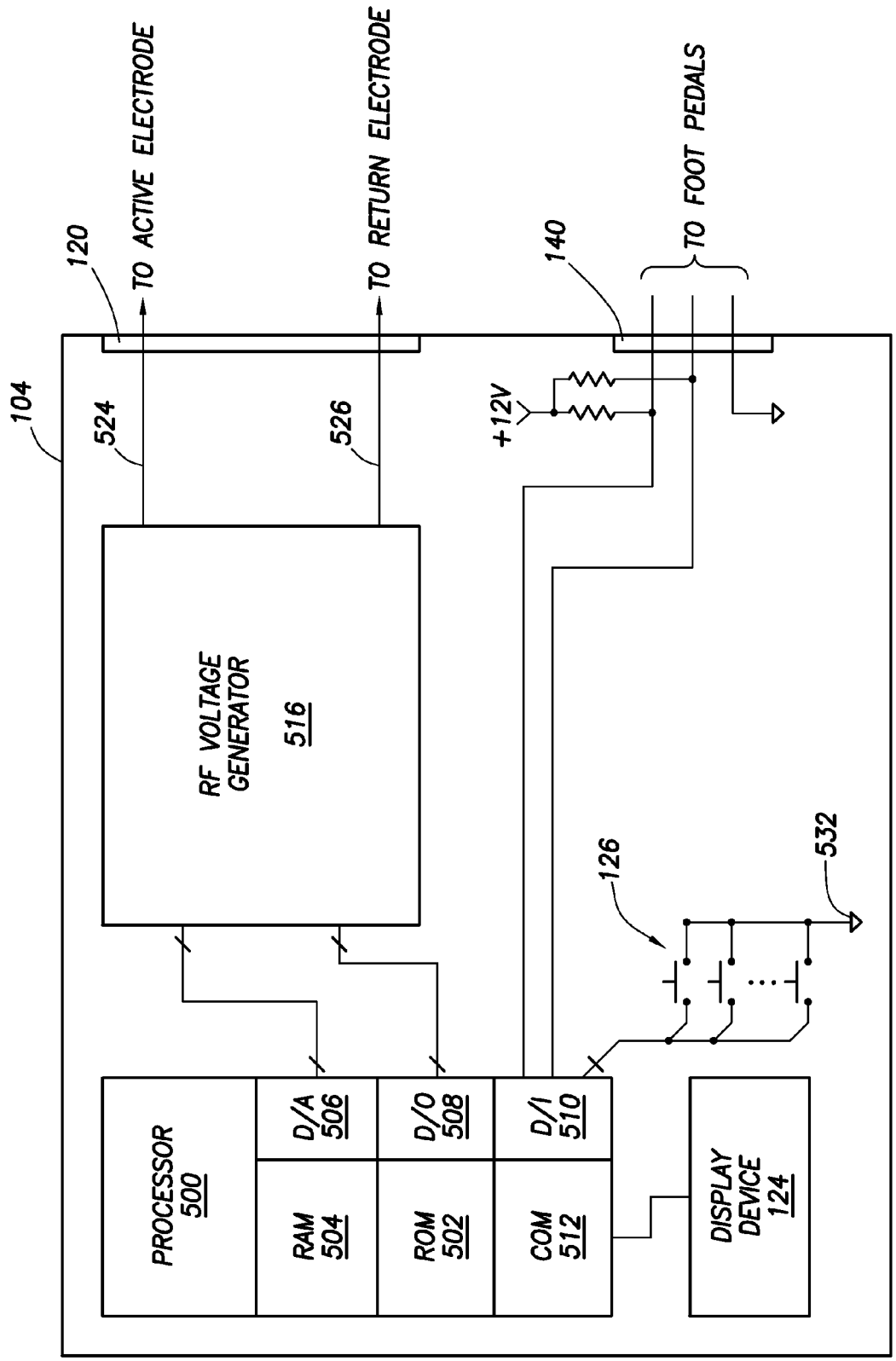
FIG. 5 shows an electrical block diagram of an electrosurgical controller in accordance with at least some embodiments.

FIG. 5 shows an electrical block diagram of controller 104 in accordance with at least some embodiments. In particular, the controller 104 comprises a processor 500. The processor 500 may be a microcontroller, and therefore the microcontroller may be integral with read-only memory (ROM) 502, random access memory (RAM) 504, digital-to-analog converter (D/A) 506, digital outputs (D/O) 508 and digital inputs (D/I) 510. The processor 500 may further provide one or more externally available peripheral busses, such as a serial bus (e.g., $I^2C$), parallel bus, or other bus and corresponding communication mode. The processor 500 may further be integral with communication logic 512 to enable the processor 500 to communicate with external devices, as well as internal devices, such as display device 124. Although in some embodiments the processor 500 may be implemented in the form of a microcontroller, in yet other embodiments the processor 500 may be implemented as a standalone central processing unit in combination with individual RAM, ROM, communication, D/A, D/O and D/I devices, as well as communication hardware for communication to peripheral components.

ROM 502 stores instructions executable by the processor 500. In particular, the ROM 502 may comprise a software program that implements the various embodiments of adjusting and/or modifying the waveform of the RF energy created by the voltage generator 516. The RAM 504 may be the working memory for the processor 500, where data may be temporarily stored and from which instructions may be executed. Processor 500 couples to other devices within the controller 104 by way of the digital-to-analog converter 506 (e.g., in some embodiment the RF generator 516), digital outputs 508 (e.g., in some embodiment the RF generator 516), digital inputs 510 (e.g., interface devices such as push button switches 126 or foot pedal assembly 130 (FIG. 1)), communication device 512 (e.g., display device 124), and other peripheral devices.

Voltage generator 516 generates an alternating current (AC) voltage signal that is applied to electrical pins in the wand connector 120 and ultimately to electrodes of the wand 102. In some embodiments, the voltage generator defines an active terminal 524 and return terminal 526. Additional active terminals and/or return terminals may be equivalently used. Each of the terminals 524 and 526 couple to electrical pins in the wand connector 120. The active terminal 524 is the terminal upon which the voltages and electrical currents are induced by the voltage generator 516, and the return terminal 526 provides a return path for electrical currents. It would be possible for the return terminal 526 to provide a common or ground being the same as the common or ground within the balance of the controller 104 (e.g., the common 532 used on push-buttons 126), but in other embodiments the voltage generator 516 may be electrically "floated" from the balance of the controller 104, and thus the return terminal 526, when measured with respect to the common or earth ground (e.g., common 532) may show a voltage; however, an electrically floated voltage generator 516 and thus the potential for voltage readings on the return terminals 528, 530 relative to earth ground does not negate the return terminal status of the terminal 526 relative to the active terminal 524.

The AC voltage signal generated and applied between an active terminal and return terminal by the voltage generator 516 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is much greater at 100 kHz. In other applications, such as procedures in or around the heart or head and neck, higher frequencies may be desirable (e.g., 400-600 kHz) to reduce low frequency current flow into the heart or the nerves of the head and neck.

The RMS (root mean square) voltage generated by the voltage generator 516 may be in the range from about 5 Volts (V) to 1800 V, in some cases in the range from about 10 V to 500 V, often between about 10 V to 400 V depending on the active electrode size, the operating frequency and the operation mode of the particular procedure or desired effect on the tissue (i.e., contraction, coagulation, cutting or ablation). The peak-to-peak voltage generated by the voltage generator 516 for ablation in some embodiments is a square waveform with a peak-to-peak voltage in the range of 10 V to 2000 V and in some cases in the range of 100 V to 1800 V and in other cases in the range of about 28 V to 1200 V, often in the range of about 100 V to 320V peak-to-peak (again, depending on the electrode size, number of electrodes the operating frequency and the operation mode). Lower peak-to-peak voltage is used for tissue coagulation, thermal heating of tissue, or collagen contraction and may be in the range from 50 V to 1500V, in some cases 100 V to 1000 V and in other cases 60 V to 130 V peak-to-peak (again, using a square waveform).

The voltage and current generated by the voltage generator 516 may be delivered in a series of voltage pulses or AC voltage with a sufficiently high frequency (e.g., on the order of 5 kHz to 20 MHz) such that the voltage is effectively applied continuously (as compared with, e.g., lasers claiming small depths of necrosis, which are pulsed about 10 Hz to 20 Hz). In addition, the duty cycle (i.e., cumulative time in any one-second interval that energy is applied) of a square wave voltage produced by the voltage generator 516 is on the order of about 50% for some embodiments as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular), as discussed more below.

The voltage generator 516 delivers average power levels ranging from several milliwatts to hundreds of watts per electrode, depending on the voltage applied to the target electrode for the target tissue being treated, and/or the maximum allowed temperature selected for the wand 102. The voltage generator 516 is configured to enable a user to select the voltage level according to the specific requirements of a particular neurosurgical procedure, cardiac surgery, arthroscopic surgery, dermatological procedure, ophthalmic procedures, open surgery, or endoscopic surgery procedure. For cardiac procedures and potentially for neurosurgery, the voltage generator 516 may have a filter that filters leakage voltages at frequencies below 100 kHz, particularly voltages around 60 kHz. Alternatively, a voltage generator 516 configured for higher operating frequencies (e.g., 300 kHz to 600 kHz) may be used in certain procedures in which stray low frequency currents may be problematic. A description of various voltage generators 516 can be found in commonly assigned U.S. Pat. Nos. 6,142,992 and 6,235,020, the complete disclosure of both patents are incorporated herein by reference for all purposes.

In accordance with at least some embodiments, the voltage generated 516 is configured to limit or interrupt current flow when low resistivity material (e.g., blood, saline or electrically conductive gel) causes a lower impedance path between the return electrode(s) and the active electrode(s). Further still, in some embodiments the voltage generator 516 is configured by the user to be a constant current source (i.e., the output voltage changes as function of the impedance encountered at the wand 102).

In some embodiments, the various operational modes of the voltage generator 516 may be controlled by the processor 500 by way of digital-to-analog converter 506. For example, the processor 500 may control the output voltages by providing one or more variable voltages to the voltage generator 516, where the voltages provided by the digital-to-analog converter 506 are proportional to the voltages to be generated by the voltage generator 516. In other embodiments, the processor 500 may communicate with the voltage generator 516 by way of one or more digital output signals from the digital output 508, or by way of packet based communications using the communication device 512 (the communication-based embodiments not specifically shown so as not to unduly complicate FIG. 5).

Figure 6:
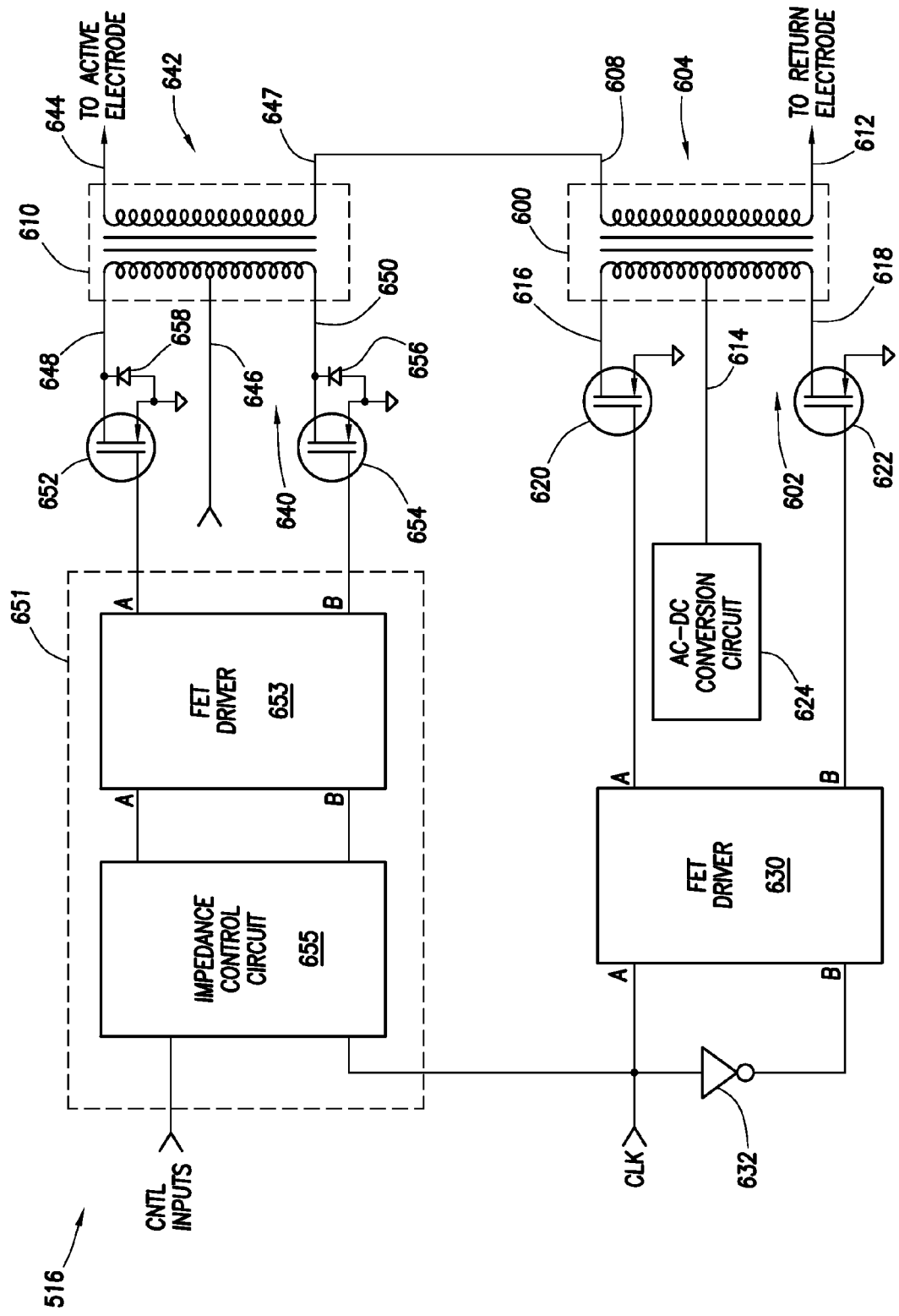
FIG. 6 shows an electrical block diagram of a voltage generator in accordance with at least some embodiments.

FIG. 6 shows at least some of the internal components of the voltage generator 516 in accordance with at least some embodiments. In particular, the voltage generator 516 comprises a main transformer 600. The main transformer 600 defines a primary winding 602 and a secondary winding 604. The secondary winding 604 has plurality of leads or terminals that couple to electrical pins of the wand connector 120 (FIG. 1). In the illustrative case of FIG. 6, the secondary winding has an active terminal 608 that couples to the active electrode (s) (by way of a control transformer 610 (discussed more below)), and return terminal 612. The primary winding 602 comprises a plurality of terminals as well as an electrical center tap (hereafter just center tap). In the illustrative case of FIG. 6, the primary winding 602 comprises terminals 616 and 618, and center tap 614. Each terminal 616 and 618 defines a respective number of turns relative to the center tap 608. In some embodiments, the number of turns defined by terminals 616 and 618 relative to the center tap 608 is approximately the same (i.e., within few turns).

Each terminal 616 and 618 is coupled to an electrically controlled switch, with the electrically controlled switches illustrated as a field effect transistors (FETs) 620 and 622, respectively. In particular embodiments, the FETs 620 and 622 are each a part number IRF540 N-Channel FET available from SGS-Thomson of Phoenix, Ariz. Though FETs are illustrated, other electrically controlled switch devices (e.g., bipolar junction transistors) may be equivalently used. The center tap 614 is coupled to an alternating current (AC) to direct current (DC) (AC-to-DC) conversion circuit 624. The AC-to-DC conversion circuit 624 takes as input AC signals (e.g., 120 V AC signal from a wall socket), and creates a fixed or selectable DC voltage that couples to the center tap 614. The voltage generator 516 in accordance with the various embodiments induces the RF energy on the secondary winding 604 by alternately forcing current from the DC signal at the center tap 614 through a portion of the primary winding in a first direction, and then forcing current from the DC signal through a portion of the primary winding in a second direction. Alternately forcing the current from the DC signal through the primary winding creates an AC signal applied to the primary winding 602, which AC signal induces voltages on the secondary winding 604.

Consider, as an explanation of using a DC signal coupled to the center tap 614 yet producing an AC primary winding signal, a positive DC signal applied at the center tap 614. Initially, for this example, FET 620 is made conductive drain-to-source while FET 622 is non-conductive. Because the source of FET 620 is coupled to ground, a current flow is induced in the portion of the primary winding 602 between the center tap 614 and the terminal 616. At a certain time thereafter, as a function of the desired frequency of the RF energy, FET 620 is made non-conductive and a short time later FET 622 is made conductive drain-to-source. The process repeats with electrical current from the AC-to-DC conversion circuit 624 alternately flowing first one direction in the primary winding 602, and then the other direction, thus creating an AC signal in the primary of the main transformer 600. The AC signal induced on the primary winding 602 by operation of the FETs 620 and 622 induces an AC voltage on the secondary winding 604, and thus AC voltages on the active terminal 608 relative to the return terminal 612. The magnitude of the voltage induced is a function of at least the magnitude of the DC voltage applied at the center tap 614 and the turn's ratio of the main transformer 600.

FIG. 6 also illustrates a driving circuit for the FETs 620 and 622. In particular, FIG. 6 shows a FET driver circuit 630 coupled to FETs 620 and 622. The FET driver circuit 630 may be a part number TC4427 available from Microchip of Chandler, Ariz. Other integrated driver circuits, and driver circuits constructed from discrete components, may be equivalently used. The clock signal (CLK) provided to the driver circuits 630 may be generated within the voltage generator 516, or may be provided from an external source, such as the processor 500. The frequency and duty cycle of the clock signal may be selected based on the particular procedure that the controller 104 is used to perform, with the selection based on user interaction with an interface device such as the buttons on the front panel of the controller 104, or the pedal system 130.

As illustrated, the "A" input of FET driver circuit 630 follows the clock signal. As the clock signal oscillates between a high voltage and a low voltage, the gate of FET 620 is driven high by the FET driver circuit 630 with each high voltage state of the clock, and low with each low voltage state of the clock. The illustrative FETs 620 and 622 are N-Channel FETs, and are thus conductive drain-to-source when a high gate voltage is present. Thus, during periods of time when FET 620 has a high gate voltage, FET 620 is conductive drain-to-source. Likewise, the "B" input of the FET driver circuit 630 follows a logical NOT of the clock signal (because the clock signal applied to FET driver 630 first passes through NOT gate 632), and the gate of FET 622 is driven high with each low voltage state of the clock signal. In this case then, the current from the DC signal alternately flows from the center tap 614 through the FET 620 and 622, and a first AC voltage signal is induced on the terminals of the secondary winding 604.

Still referring to FIG. 6, as an additional mechanism to implement voltage control of the AC signal applied to the active and return electrodes, a control transformer 610 is electrically coupled to the main transformer 604. The control transformer is implemented as a selectable impedance device. In particular, when a lower voltage AC signal is desired on the active electrode(s) relative to the return electrode(s), the impedance the AC signal experiences across the control transformer is increased and thus the AC signal experiences a higher voltage drop resulting in less voltage applied to the electrodes of the wand. Likewise, when a higher voltage AC signal is desired on the active electrode(s) relative to the return electrode(s), the impedance the AC signal experiences across the control transformer is decreased and thus the AC signal experiences a lower voltage drop resulting in more voltage applied to the electrodes of the wand. In some embodiments, the selective control of the impedance may be completely within a half-cycle of the AC signal. Stated otherwise, in particular embodiments the impedance changes experienced by the AC signal through the control transformer 610 may be applied and rescinded within a half-cycle (half a period of the frequency of the AC signal). Application and rescission of impedance changes within a single half-cycle are significantly faster than changes that may be implemented by way of, for example, changing the DC voltage applied to the center tap 614 of the main transformer 600. Selective control of the impedance experienced by the AC signal may take many forms, and each will be discussed in turn, starting with on-off control of electrically controlled switches coupled to a winding of the control transformer.

Control transformer 610 comprises a first winding 640 and a second winding 642. As illustrated, and in particular embodiments, the control transformer 610 is identical to the main transformer 600; however, other non-identical transformers may be equivalently used. The second winding 642 defines two terminals 644 and 647. As illustrated, the second winding 642 couples in series with the secondary winding 604 of the main transformer 600. The first winding 640 comprises terminals 648 and 650, along with center tap 646. Each terminal 648 and 650 defines a respective number of turns relative to the center tap 646. In some embodiments, the number of turns defined by terminals 648 and 650 relative to the center tap 646 is approximately the same (i.e., within few turns).

Each terminal 648 and 650 is coupled to an electrically controlled switch, the electrically controlled switch for each tap illustrated as FETs 652 and 654, respectively. In particular embodiments, the FETs 652 and 654 are part number IRF540 N-channel FETs. Though FETs are illustrated, other electrically controlled switch devices (e.g., bipolar junction transistors) may be equivalently used. The center tap 646 may be grounded, coupled to a voltage source, or electrically floated. For now, assume the center tap 646 is electrically floated. FIG. 6 also illustrates a control circuit 651 for driving the FETs 648 and 650. In particular, the control circuit 651 comprises a FET driver circuit 653 coupled to FETs 648 and 650. The FET driver circuit 653 may also be a part number TC4427 discussed above. Other integrated driver circuits, and driver circuits constructed from discrete components, may be equivalently used. The "A" and "B" inputs of FET driver circuit 653 are driven by impedance control circuit 655. Thus, in the particular embodiments, under control of the impedance control circuit 655, the FETs 652 and 654 are driven between an off-state and a fully-conductive (i.e., saturated) state based on the state of the control inputs to the FET driver circuit 653.

In order to describe embodiments where the FETs 652 and 654 are used as on-off devices, consider first a situation where both FETs 652 and 654 are non-conductive. In the state where FETs 652 and 654 are non-conductive, no electrical current flows in the first winding 640 and the impedance exhibited by the second winding 642 of the control transformer is at a high or maximum value. Thus, the AC voltage signal from the main transformer 600 (which voltage signal may be referred to as an intermediate AC voltage signal) propagates through the second winding 642 of the control transformer 610 and experiences a voltage drop based on the impedance of the second winding 642. The intermediate AC voltage signal, after experiencing the voltage drop across the second winding 642, may be referred to as the final AC voltage signal, as it is such signal that is applied to the pins of the connector 120 and ultimately the electrodes of the electrosurgical wand 102.

Now consider the situation where the FETs 652 and 654 are fully conductive, and thus electrical current is free to flow in the first winding 640 of the control transformer. In such an illustrative situation, electrical current flow in the second winding 642 induces voltage and current in the first winding 640. In particular, during a first or positive half-cycle of the AC voltage signal (and considering the center tap 646 electrically floated), the electrical current flow in the second winding 642 induces a voltage and electrical current in the first winding 640 proportional to the turns ratio of the transformer. The electrical current in the first half-cycle may flow through the shorting diode 656, through the first winding 640, and then through the FET 652 to ground or common. During a second or negative half-cycle of the AC voltage signal, the electrical current flow in the second winding 642 again induces a voltage and electrical current in the first winding 640 proportional to the turns ratio of the transformer, but with opposite polarity. The electrical current in the second half-cycle may flow through the shorting diode 658, through the first winding 640, and then through the FET 654 to ground or common. Thus, during each half-cycle the first winding 640 is effectively electrically shorted at its terminals 648 and 650. During each half-cycle, the electrical current induced in the first winding 640 lowers the impedance exhibited by the second winding 642. Thus, in propagating from the main transformer 600 through the second winding 642 of the control transformer 610, the AC voltage signal generated by the main transformer 600 experiences its lowest voltage drop across the second winding 642 (thereby creating the final AC voltage signal) before being applied to the active electrode.

The various embodiments discussed to this point have assumed that the FETs 652 and 654 are either non-conductive for extended periods of time (at least a half-cycle of the AC voltage signal), or conductive for extended periods of time. Operating the FETs in such a manner provides a two-state control of the final AC voltage signal applied to the active electrode(s) relative to the return electrode(s). However, in other embodiments the FETs 652 and 654 associated with the first winding 640 may be made conductive and then non-conductive within a half-cycle, and in some cases multiple times within a half-cycle. Consider first a situation where the physician using the electrosurgical controller desires to apply a waveform to the electrodes of the electrosurgical wand 102 that has a leading-edge spike.

Figure 7:
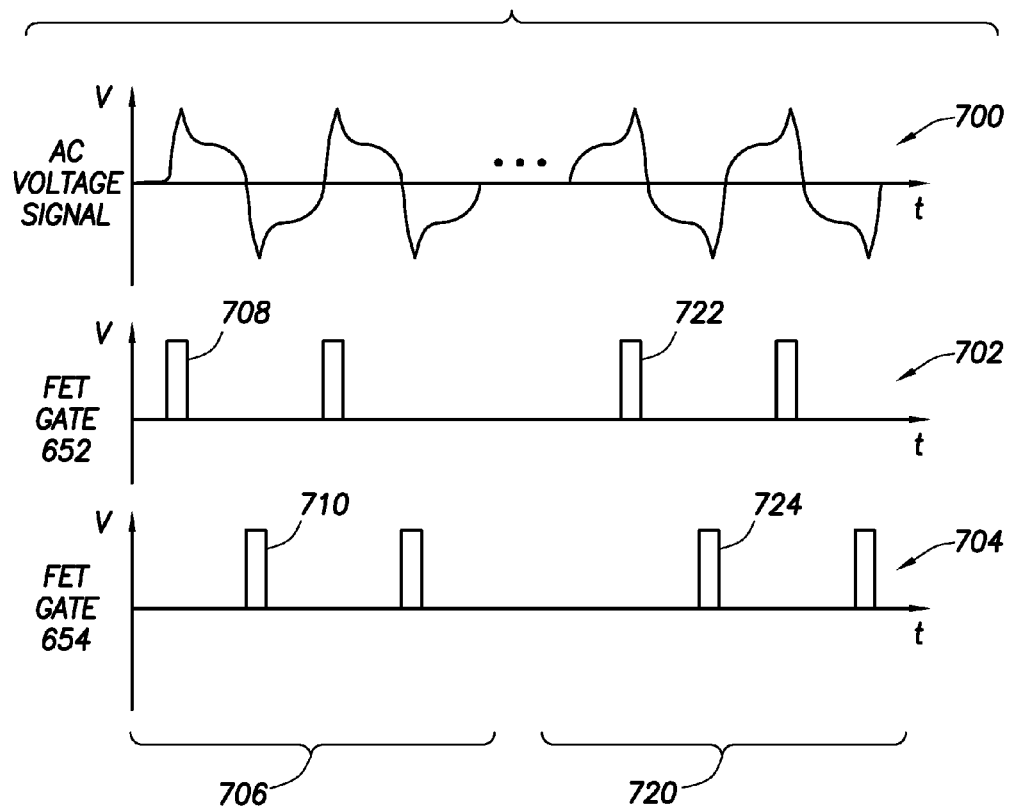
FIG. 7 shows a plurality of plots in accordance with at least some embodiments.

FIG. 7 shows a plurality of waveforms, each plotted on a different ordinate axis, but with corresponding time. In particular, plot 700 shows a plurality of possible AC voltage signals applied to the electrodes of a wand, plot 702 shows gate voltage for FET 652 assuming a N-channel FET, and plot 704 shows a gate voltage for FET 654 assuming a N-channel FET. Time period 706 illustrates the waveform having leading edge spikes, along with the gate voltages for FETs 652 and 654 to achieve the spikes. In particular, during the positive half-cycle gate voltage pulse 708 makes illustrative FET 652 conductive, and thus the impedance across the second winding 642 of control transformer 610 low. In such a situation, the voltage drop across the second winding 642 is low, and thus initially the voltage applied to the active electrode(s) relative to the return electrode(s) is relatively high. However, after the leading edge spike, but still within the half-cycle, the gate voltage drops to zero, and thus FET 652 becomes non-conductive. A non-conductive FET 652 results in higher impedance exhibited by the second winding 642 of the control transformer, a larger voltage drop across the second winding 642, and thus the AC voltage signal applied to the electrodes drops.

Still referring to FIG. 7, in the immediately subsequent (i.e., negative) half-cycle, the gate voltage for FET 652 remains zero, the gate voltage pulse 710 makes illustrative FET 654 conductive, and thus the impedance across the second winding 642 of control transformer 610 again becomes low. The voltage drop across the second winding 642 is low, and thus initially the voltage applied to the active electrode(s) relative to the return electrode(s) is a relatively large negative value. However, after the leading edge spike, but still within the second half-cycle, the gate voltage for FET 654 drops to zero, and thus FET 654 becomes non-conductive. A non-conductive FET 654 results in higher impedance exhibited by the second winding 642 of the control transformer, a larger voltage drop across the second winding 642, and thus the AC voltage signal applied to the electrodes become less negative. Thereafter, the cycle may repeat as shown.

Now consider a situation where the physician using the electrosurgical controller 104 desires to apply a waveform to the electrodes of the electrosurgical wand 102 that has a trailing-edge spike. FIG. 7, particularly the plots in time frame 720, show the AC voltage signal with trailing edge spikes, as well as gate voltage for the FETs 652 and 654 to achieve the spikes. In particular, during an initial portion of a first half-cycle, the gate voltage for FET 652 is low and thereafter, but within half-cycle, the gate voltage pulse 722 makes illustrative FET 652 conductive. Thus the impedance across the second winding 642 of control transformer 610 is initially high, and then transitions to low impedance within the half-cycle, thus creating a voltage spike at the end of the waveform within the half-cycle. During an initial portion of a second or negative half-cycle, the gate voltage for FET 652 is low and the gate voltage for FET 654 is also initially low. Thereafter, but within the half-cycle, the gate voltage pulse 724 makes illustrative FET 652 conductive. Thus the impedance across the second winding 642 of control transformer 610 is initially high, and then transitions to low impedance within the half-cycle, thus creating a voltage spike at the end of the waveform within the negative half-cycle.

Figure 8:
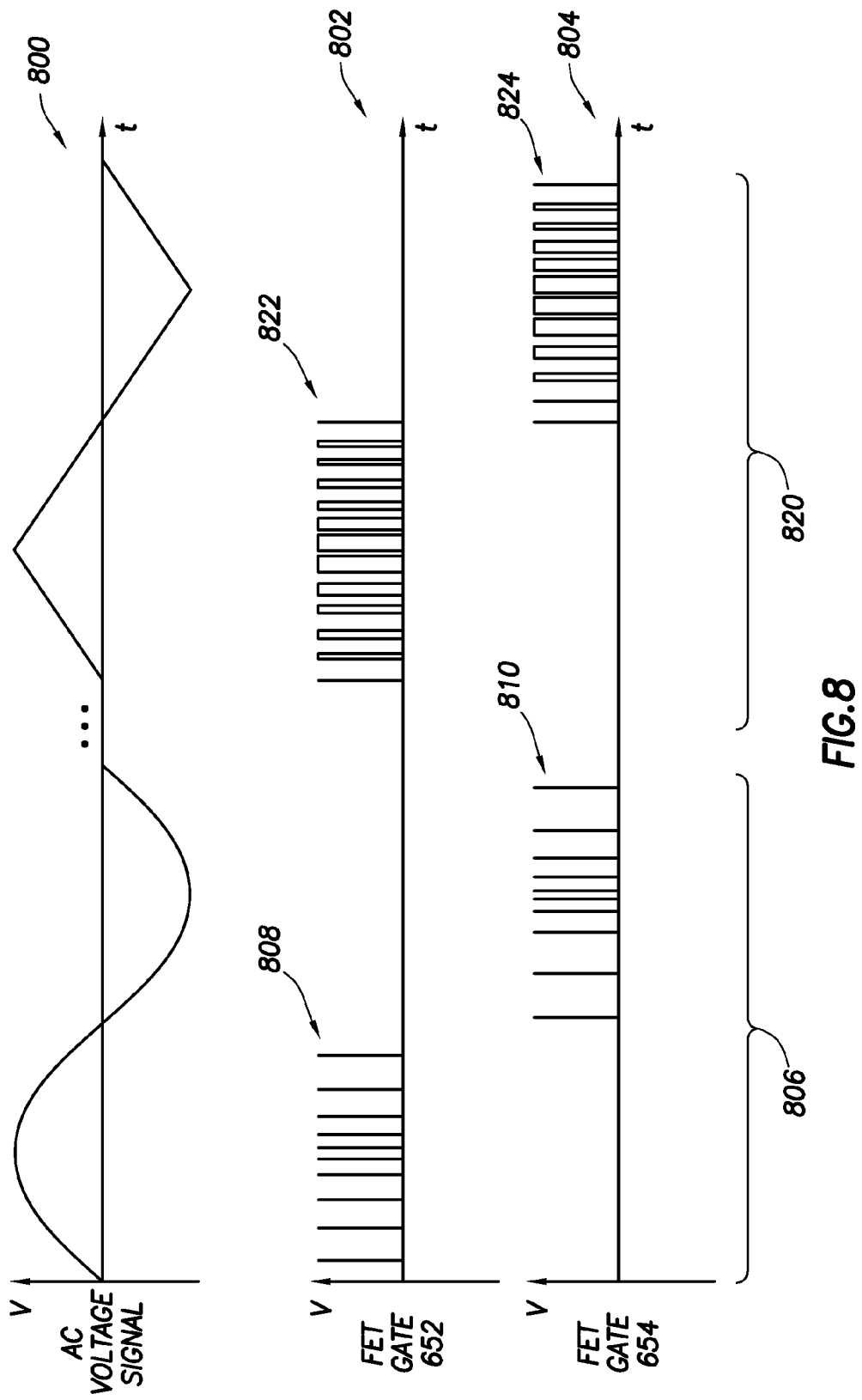
FIG. 8 shows a plurality of plots in accordance with at least some embodiments.

Now consider a situation where the physician using the electrosurgical controller 104 desires to apply a waveform to the electrodes that is more sinusoidal. FIG. 8 shows a plurality of waveforms, each plotted on a different ordinate axis, but with corresponding time. In particular, plot 800 shows a plurality of possible AC voltage signals applied to the electrodes of a wand, plot 802 shows gate voltage for FET 652 assuming a N-channel FET, and plot 804 shows a gate voltage for FET 654 assuming a N-channel FET. Time period 806 illustrates a substantially sinusoidal waveform, along with the gate voltage pulses for FETs 652 and 654 to achieve the substantially sinusoidal waveform. In particular, the time period 806 illustrates not only wave-shaping of the AC voltage signal, but also wave shaping by changing the frequency of the pulses applied to the FETs 652 and 654. Assuming a constant duty cycle, during the positive half-cycle, the frequency of the voltage pulses 808 applied to the gate of FET 652 are initially relatively low, increase toward the middle of the half-cycle, and decrease toward the end of the half-cycle. Thus, initially the average impedance of the second winding 642 is high (large voltage drop and thus lower voltage applied to the electrodes), the average impedance increases toward the middle of the half-cycle (lower voltage drop and thus higher voltage applied to the electrodes), and the average impedance decreases toward the end of the half-cycle (large voltage drop and thus lower voltage applied to the electrodes). Likewise for the negative half-cycle in the time period 806, the frequency of the voltage pulses 810 applied to the gate of FET 654 are initially relatively low, increase toward the middle of the half-cycle, and decrease toward the end of the half-cycle. Thus, initially the average impedance of the second winding 642 is high (large voltage drop and thus lower voltage applied to the electrodes), the average impedance increases toward the middle of the half-cycle (lower voltage drop and thus higher voltage applied to the electrodes), and the average impedance decreases toward the end of the half-cycle (large voltage drop and thus lower voltage applied to the electrodes).

Now consider a situation where the physician using the electrosurgical controller 104 desires to apply a waveform to the electrodes that is triangular. Time period 820 illustrates the waveform having a substantially triangular wave form, along with the gate voltage pulses for FETs 652 and 654 to achieve the substantially triangular waveform. In particular, the time period 806 illustrates not only wave-shaping of the AC voltage signal, but also wave shaping by changing the duty cycle of the pulses applied to the FETs 652 and 654. During the positive half-cycle, the frequency of the voltage pulses 822 applied to the gate of FET 652 is constant and the duty cycle is initially very low. The duty cycle increases linearly toward the middle of the half-cycle, and decrease linearly toward the end of the half-cycle. Thus, initially the average impedance of the second winding 642 is high (large voltage drop and thus lower voltage applied to the electrodes), the impedance increases toward the middle of the half-cycle (lower voltage drop and thus higher voltage applied to the electrodes), and the impedance decreases toward the end of the half-cycle (large voltage drop and thus lower voltage applied to the electrodes). Likewise for the negative half-cycle in the time period 820, the frequency of the voltage pulses 824 applied to the gate of FET 654 is constant and the duty cycle is initially very low. The duty cycle increases linearly toward the middle of the half-cycle, and decrease linearly toward the end of the half-cycle. Thus, initially the average impedance of the second winding 642 is high (large voltage drop and thus lower voltage applied to the electrodes), the impedance increases toward the middle of the half-cycle (lower voltage drop and thus higher voltage applied to the electrodes), and the impedance decreases toward the end of the half-cycle (large voltage drop and thus lower voltage applied to the electrodes).

Although FIG. 8 illustrates controlling frequency (with constant duty cycle) with respect to a substantially sinusoidal wave-shaping, and controlling duty cycle (with constant frequency) with respect to a substantially triangular wave-shaping, such is only illustrative. Duty cycle could likewise be used in the sinusoidal wave-shaping, and frequency of the pulses could be used in the triangular wave-shaping. Moreover, a combination of controlling both frequency and duty cycle may be implemented. Furthermore, the sinusoidal and triangular are merely illustrative, and any wave shape may be created by selective control of the impedance of the second winding 642.

Figure 9:
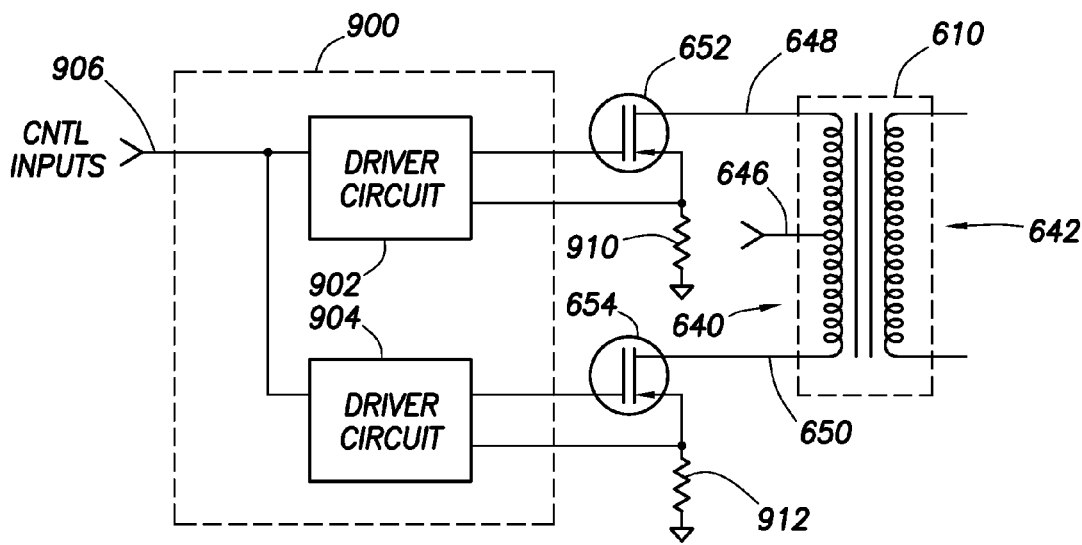
FIG. 9 shows another embodiment of the control transformer and related circuitry in accordance with at least some embodiments.

The various embodiments discussed to this point have assumed on-off control (i.e., driving the FETs between non-conductive and saturated states) of the illustrative FETs 652 and 654 to control the impedance of the second winding 642, and thus the voltage drop and wave-shaping characteristics thereof. However, in other embodiments the FETs may be used in their active regions. FIG. 9 illustrates a portion of the voltage generator 516 including the control transformer 610, FETs 652 and 654, along with active driver circuit 900. The active driver circuit 900 comprises a driver circuit 902 coupled to FET 652, and a driver circuit 904 coupled to FET 654. The driver circuits 902 and 904 take commands from the control inputs 906, which may originate within the voltage generator 516, or may originate with the processor 500. Although it may be possible to drive the FETs 652 and 654 to their active regions in an open-loop sense (i.e., without feedback), in particular embodiments the driver circuits 902 and 904 receive feedback by reading a voltage across resistors 910 and 912, respectively, coupled between the FETs 652 and 654, respectively, and ground or common. Other feedback mechanisms may be equivalently used. Thus, rather than using the FETs 652 and 654 as on-off devices, the embodiments of FIG. 9 drive the FETs 652 and 654 into their active region in respective half-cycles, thus actively controlling the amount of current in the first winding 640.

Consider, for example, that the circuit of FIG. 9 is utilized to create the substantially sinusoidal waveform of time period 806 in FIG. 8. During the initial portion of the positive half-cycle, driver circuit 902 drives the FET 652 to be either non-conductive or only slightly conductive. As the positive half-cycle progresses, the driver circuit 902 drives the FET 652 to be more conductive, and then in the waning portion of the positive half-cycle the driver circuit 902 drives the FET 652 to be either non-conductive or only slightly conductive. The point is, during a portion of the half-cycle, the FET 652 is utilized in its active region for extended amounts of time, and not as a merely a transition between the non-conductive and saturated states. During the initial portion of the negative half-cycle, driver circuit 904 drives the FET 654 to be either non-conductive or only slightly conductive. As the negative half-cycle progresses, the driver circuit 904 drives the FET 654 to be more conductive, and then in the waning portion of the negative half-cycle the driver circuit 904 drives the FET 654 to be either non-conductive or only slightly conductive. Here again, during a portion of the negative half cycle, the FET 654 is utilized in its active region for extended amounts of time, and not as a merely a transition between the non-conductive and saturated states.

Figure 10:
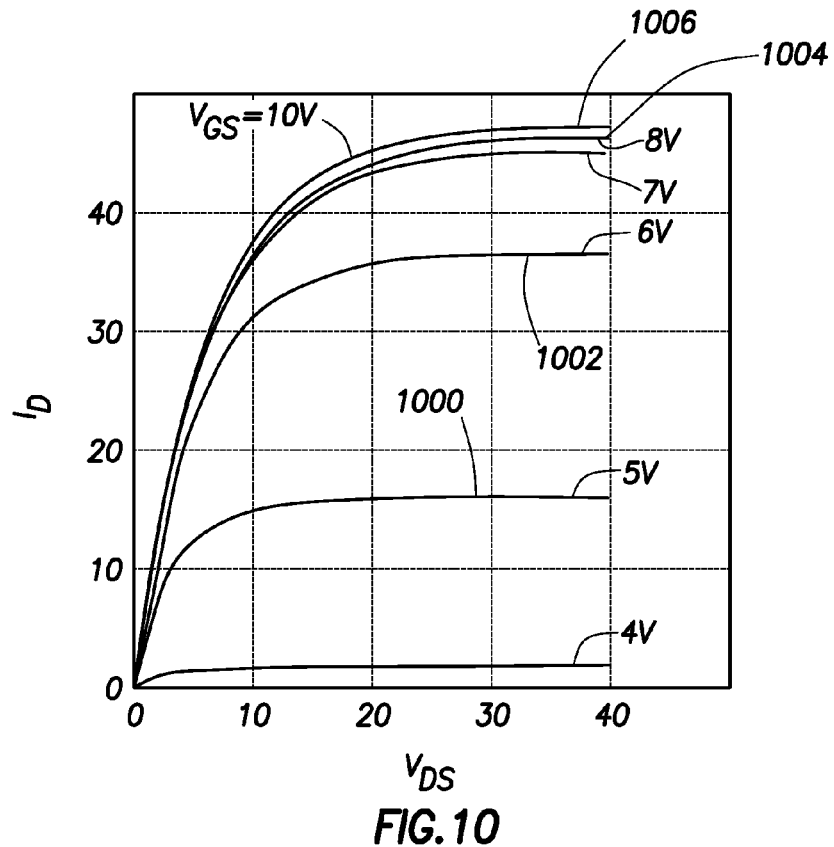
FIG. 10 shows an illustrative transistor curve.

In order to more fully define the active region as opposed to saturation, attention is now directed to FIG. 10. In particular, FIG. 10 shows a transistor curve for the illustrative IRF540 N-Channel FET. The abscissa axis is the voltage drain-to-source ($V_{DS}$), the ordinate axis is the current through the drain ($I_D$), and the multiple curves within the plot are based on varying gate-to-source voltage ($V_{GS}$). As shown in FIG. 10, in transitions between lower gate-to-source voltage $V_{GS}$ to higher gate-to-source voltage $V_{GS}$, at lower voltage levels changes result in significant changes in drain current $I_D$. For example, a change in gate-to-source voltage $V_{GS}$ from 5 V (curve 1000) to 6 V (curve 1002) results in more than doubling of the gate current $I_D$ from about 15 amps to about 37 amps. However, as the drain current $I_D$ increases, the effect of increasing gate-to-source voltage $V_{GS}$ has less effect on drain current $I_D$. For example, a change in gate-to-source voltage $V_{GS}$ between 8 V (curve 1004) and 10 V (curve 1006) results in an increase in gate current of only a few amps. In some transistors, beyond a particular gate-to-source voltage $V_{GS}$, increase have no effect on drain current $I_D$. When changes in gate-to-source voltage result in no appreciable changes in drain current, the transistor is said to be saturated. Thus, for purposes of this disclosure and the claims, when a transistor is said to be operating in the active region, the transistor is operated within a region where changes in gate-to-source voltage (or base current for junction transistors) has an appreciable effect on drain current (emitter current for junction transistors). Temporary or fleeting presence in the active region while transitioning between a non-conductive state and a saturated stated for on-off control shall not be considered operation within the active region.

Stated otherwise, with respect to on-off control versus active region control, operation of the FETs in the active region is distinguished from operation of the FETs in the saturated region by virtue of the means used to control and regulate the average current through the FET. In the case of active control, the system makes use of the linear region of operation of the FET, whereby the slope of the ratio of the drain current to the drain to source voltage ($I_D/V_{DS}$) is determined by value of the gate to source voltage, $V_{GS}$. In this operating mode, either the average value of the current delivered through the FET or the profile of the current waveform delivered through the FET can be regulated by a variation in $V_{GS}$, provided that the gate to source voltage is maintained below the point where the drain current becomes mostly constant, or independent of the drain to source voltage. When the FETs are operated in the saturated region, the drain current is for the most part independent of the drain to source voltage, and the FET operates as a type of electrical switch. In this mode of operation, the average current delivered through the FET, or the profile of the current waveform delivered through the FET, is regulated by an adjustment or variation in the time where the FET is either saturated or non-conductive. Those skilled in the art will appreciate that during the transition between the non-conductive state and the saturated state, that the FET will by necessity pass through the active region of operation. However, this period of time where the FET is in this mode is not intended to provide a regulation of the delivered current.

Figure 11:
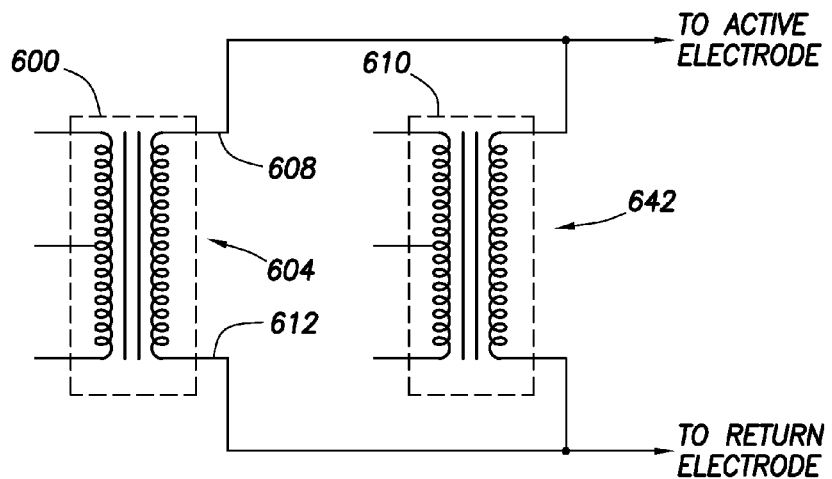
FIG. 11 shows coupling the main transformer and the control transformer in parallel in accordance with at least some embodiments.

The various embodiments discussed to this point have assumed that the main transformer 600 and the control transformer 610 are coupled in series. However, other coupling arrangements are possible. FIG. 11 shows the main transformer 600 coupled in parallel with the control transformer 610. The arrangement of FIG. 11 may likewise implement wave-shaping of the AC voltage signal applied to the active electrode(s) relative to the return electrode(s). In particular, the main transformer 610 has finite power transfer capabilities such that changes in impedance of the second winding 642 may result in increased current flow and thus decreased voltage across the terminals 608, 612. Thus, in the illustrated embodiments wave-shaping takes place by changing the AC current flow through the second winding 642, with decreased impedance resulting in increased current flow through the second winding 642. Increased current flow in combination with the current supplied to the electrodes may result in decreased voltage on the secondary winding 604. The opposite is also true, with decreased impedance on the second winding 642 resulting in lower current flow from the secondary winding 604 and thus increased voltage.

Figure 12:
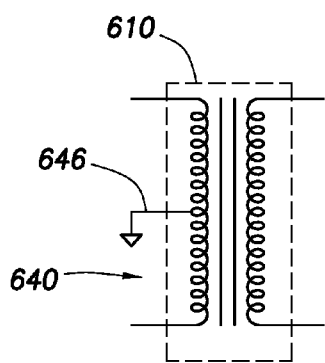
FIG. 12 shows embodiments with the center tap of the control transformer coupled to ground or common.
Figure 13:
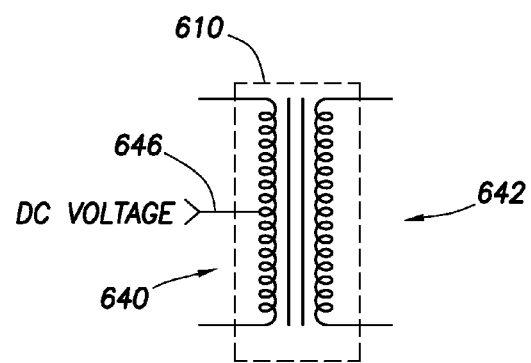
FIG. 13 shows embodiments with the center tap of the control transformer coupled to a DC voltage.

Moreover, the various embodiments described to this point have assumed that the center tap 646 of the control transformer is electrically opened or floated. However, the center tap need not be floated. For example, FIG. 12 illustrates the control transformer 610 with the center tap 646 of the first winding 640 coupled to ground or common. In such a situation, the shorting diodes 656 and 658 (FIG. 6) may be omitted, and/or transistors without internal shorting diodes may be used. FIG. 13 illustrates the situation where the center tap 646 is coupled to a DC voltage (e.g., one or two volts). In the embodiments of FIG. 13, electrical current in the first winding 640 is not only that induced by the second winding 642, but also as flows from the DC voltage source when the FETs 652 and 654 (not shown in FIG. 12) are conductive, with greater current flow in the first winding 640 the impedance of the second winding is further reduced.

The various embodiments discussed to this point have assumed a fixed voltage DC signal at the center tap 614 of the main transformer 600 (FIG. 6). Thus, in spite of the fixed voltage DC signal at the center tap 614 on the primary winding 602, multiple output voltages on the active electrode(s) of the wand 102 may be achieved by control of the impedance of the control transformer 610. Having a fixed voltage DC signal created by the AC-to-DC converter circuit 624 enables voltage generator 516 to have a relatively simple (and inexpensive) construction. In yet still further embodiments, the AC-to-DC conversion circuit 624 creates selectable voltage DC signals to apply to the center tap 614, and thus the voltage provided to the active electrode(s) relative the return electrode(s) may be controlled not only by the impedance of the control transformer 610, but also the DC voltage applied to the center tap 614, thus enabling a broader range of control for the output voltages. The selectable DC voltage created by the AC-to-DC conversion circuit 624 could be created at the command of the processor 500 (such as commands sent by way of an analog signal from the D/A port 506, or one or more digital signals from the D/O port 508, or both) or by a circuit within voltage generator 516 (not shown so as not to unduly complicate the figure).

Figure 14:
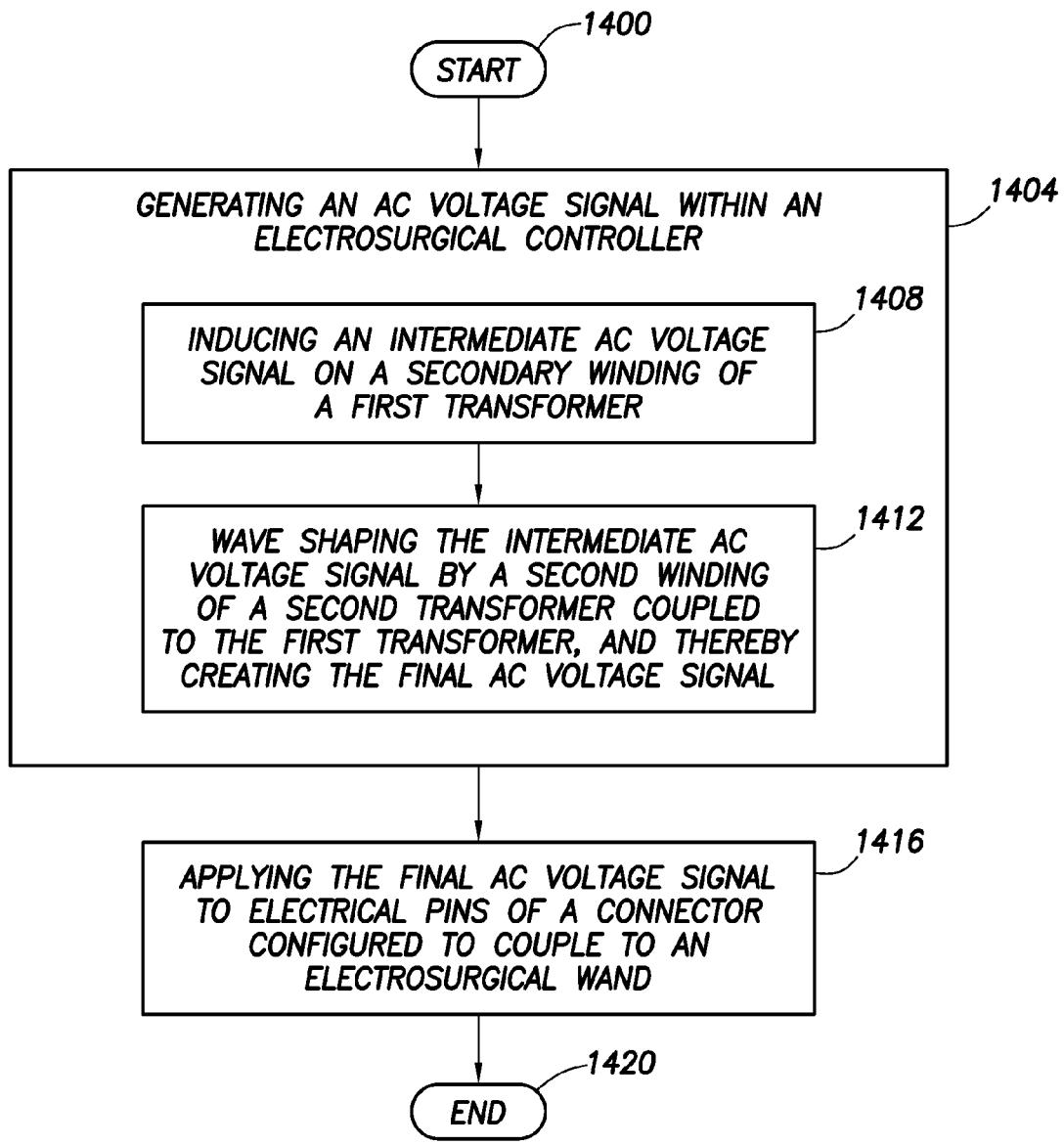
FIG. 14 shows a method in accordance with at least some embodiments.

FIG. 14 illustrates a method in accordance with at least some embodiments. In particular, the method starts (block 1400) and proceeds to generating an AC voltage signal within an electrosurgical controller (block 1404). In some embodiments, the generating comprises inducing an intermediate AC voltage signal on a secondary winding of a first transformer (block 1408), and wave shaping the intermediate AC voltage signal by a second winding of a second transformer coupled to the first transformer (and thereby creating the final AC voltage signal) (block 1412). Thereafter, the illustrative method involves applying the final AC voltage signal to electrical pins of a connector configured to couple to an electrosurgical wand (block 1416), and the illustrative method ends (block 1420).

While preferred embodiments of this disclosure have been shown and described, modifications thereof can be made by one skilled in the art without departing from the scope or teaching herein. The embodiments described herein are exemplary only and are not limiting. For example, the various FETs associated with of the control circuit 680 are illustrated as N-Channel FETs; however, P-Channel FETs, bipolar junction transistors and in some cases solid state relays may be equivalently used. Moreover, while the wave-shaping described has been as applied equally to both the positive half-cycle and negative half-cycle of the AC voltage signal, in other embodiments the wave-shaping may be applied in different magnitudes as between the positive half-cycle and negative half-cycle, and thus the final AC voltage signal applied to the electrodes of the electrosurgical wand may have a DC bias. Because many varying and different embodiments may be made within the scope of the present inventive concept, including equivalent structures, materials, or methods hereafter though of, and because many modifications may be made in the embodiments herein detailed in accordance with the descriptive requirements of the law, it is to be understood that the details herein are to be interpreted as illustrative and not in a limiting sense.

What is claimed is:

1. An electrosurgical controller comprising:
   a wand connector configured to couple to a connector of an electrosurgical wand, the wand connector comprising a plurality of electrical pins;
   a voltage generator comprising:
     a first transformer comprising a primary winding and a secondary winding, wherein the secondary winding defines a first terminal coupled to a first electrical pin of the plurality of electrical pins of the wand connector and a second terminal coupled to a second electrical pin of the plurality of electrical pins of the wand connector;
     a second transformer, different than the first transformer, the second transformer comprises a first winding and a second winding, wherein the second winding of the second transformer is coupled to the secondary winding of the first transformer;
   wherein the electrosurgical controller is configured to modify voltage of an alternating current (AC) signal induced on the secondary winding and applied to the first electrical pin relative to the second electrical pin by selective control of an impedance of the second winding of the second transformer.

2. The electrosurgical controller of claim 1 wherein the electrosurgical controller is configured to modify the AC signal within only a portion of each half cycle of the AC signal.

3. The electrosurgical controller of claim 1 further comprising:
   the first winding of the second transformer defines a first terminal and a second terminal;
   an electrically controlled switch coupled to the first terminal of the first winding of the second transformer, wherein electrical current flow in the first winding is also configured to flow through the electrically controlled switch; and
   wherein the impedance of the second winding of the second transformer is controlled by selective control of the electrical current flow through the electrically controlled switch.

4. The electrosurgical controller of claim 3 further comprising:
   wherein the electrically controlled switch is a transistor;
   a control circuit coupled to the transistor; and
   wherein the control circuit is configured to drive the transistor between a conductive state and an off state at a frequency, and the impedance of the second winding is proportional to the frequency.

5. The electrosurgical controller of claim 3 further comprising:
   wherein the electrically controlled switch is a transistor;
   a control circuit coupled to the transistor; and
   wherein the control circuit is configured to drive the transistor between a conductive state and an off state with a duty cycle, and the impedance of the second winding is proportional to the duty cycle.

6. The electrosurgical controller of claim 3 further comprising:
   wherein the electrically controlled switch is a transistor;
   a control circuit coupled to the transistor; and
   wherein the control circuit is configured to drive the transistor to a state within an active region of the transistor, and the impedance of the second winding is proportional to the electrical current flow through the transistor.

7. The electrosurgical controller of claim 1 wherein the second winding of the second transformer is coupled in series with the secondary winding of the first transformer.

8. The electrosurgical controller of claim 1 wherein the second winding of the second transformer is coupled in parallel with the secondary winding of the first transformer.

9. The electrosurgical controller of claim 1 further comprising:
   the first winding of the second transformer defines a first terminal and a second terminal;
   a first transistor coupled to the first terminal;
   a second transistor, different than the first transistor, coupled to the second terminal;
   a control circuit coupled to the first and second transistors, wherein the control circuit is configured to force the first transistor to a conductive state during a positive half cycle of the AC signal induced on the secondary winding, and the control circuit is configured to force the second transistor to a conductive state during a negative half cycle of the AC signal; and
   wherein the impedance of the second winding during the positive half cycle is proportional to electrical current flow through the first transistor; and the impedance of the second winding during the negative half cycle is proportional to the electrical current flow through the second transistor.

10. The electrosurgical controller of claim 9 wherein the electrosurgical controller is configured to modify the AC signal applied to the first electrical pin relative to the second electrical pin such that the AC signal has a direct current (DC) bias.

11. The electrosurgical controller of claim 1 wherein the first winding of the second transformer further comprises a center tap, and wherein the center tap is electrically floated.

* * * * *